(12) United States Patent
Efremkin

(10) Patent No.: US 11,737,778 B2
(45) Date of Patent: Aug. 29, 2023

(54) DEVICES AND METHODS FOR INTRABODY SURGERY

(71) Applicant: Pavel V. Efremkin, Tarrytown, NY (US)

(72) Inventor: Pavel V. Efremkin, Tarrytown, NY (US)

(*) Notice: Subject to any disclaimer, the term of this patent is extended or adjusted under 35 U.S.C. 154(b) by 164 days.

(21) Appl. No.: 17/495,566

(22) Filed: Oct. 6, 2021

(65) Prior Publication Data

US 2022/0022912 A1 Jan. 27, 2022

Related U.S. Application Data

(60) Division of application No. 16/406,683, filed on May 8, 2019, now Pat. No. 11,141,185, which is a
(Continued)

(51) Int. Cl.
*A61B 17/32* (2006.01)
*A61B 17/3207* (2006.01)
(Continued)

(52) U.S. Cl.
CPC .. *A61B 17/320725* (2013.01); *A61B 17/1659* (2013.01); *A61B 17/1615* (2013.01);
(Continued)

(58) Field of Classification Search
CPC ........ A61B 17/320725; A61B 17/1659; A61B 17/1615; A61B 17/16; A61B 17/1626; A61B 17/1631; A61B 2017/1651; A61B 2017/22079; A61B 2017/320716; A61B 2017/320775; A61B 2217/005; A61B 2018/00279; A61B 2018/00404; A61B 2018/00434; A61B 2018/00589; A61B 2218/002; A61B 2218/007; A61B 2017/00336; A61B 17/2202; A61B 18/1492; A61B 2017/00026; A61B 2017/00084; A61B 2017/00685; A61B 2017/1602; A61B 2017/22038; A61B 2017/320004; A61B 2017/320766; A61B 2018/00196; A61B 2018/00291;
(Continued)

(56) References Cited

U.S. PATENT DOCUMENTS

2002/0007190 A1* 1/2002 Wulfman ....... A61B 17/320758
606/171

* cited by examiner

*Primary Examiner* — Amanda K Hulbert
*Assistant Examiner* — Natasha Patel
(74) *Attorney, Agent, or Firm* — Lawrence G. Fridman, Esq; Feigin & Fridman, LLC

(57) ABSTRACT

A device for intrabody surgery comprises a cutting arrangement rotatable by a hollow driveshaft, which is formed by a hollow front cutting region and a rear region. The front region includes multiple longitudinal drilling sections interconnected by transversely oriented cutting blade sections. The drilling sections are positioned at an angle to each other defining in combination with the cutting blades a conically shaped grid formation having a hollow internal cavity. The grid formation defines a plurality of ports between the drilling sections and the blades. A low-pressure zone is formed within the hollow internal cavity, wherein cut occlusion materials are aspired by the low-pressure zone through the plurality of ports into the hollow internal cavity for further evacuation from the cutting arrangement.

13 Claims, 11 Drawing Sheets

Related U.S. Application Data continuation-in-part of application No. 16/192,781, filed on Nov. 15, 2018, now abandoned.

(60) Provisional application No. 62/680,260, filed on Jun. 4, 2018, provisional application No. 62/586,654, filed on Nov. 15, 2017.

(51) Int. Cl.
*A61B 17/16* (2006.01)
*A61B 17/22* (2006.01)

(52) U.S. Cl.
CPC ....... *A61B 17/1626* (2013.01); *A61B 17/1631* (2013.01); *A61B 2017/1651* (2013.01); *A61B 2017/22079* (2013.01); *A61B 2017/320716* (2013.01); *A61B 2017/320775* (2013.01); *A61B 2217/005* (2013.01)

(58) Field of Classification Search
CPC ........... A61B 2018/00452; A61B 2018/00577; A61B 2018/00601; A61B 2217/007; A61B 17/320758
See application file for complete search history.

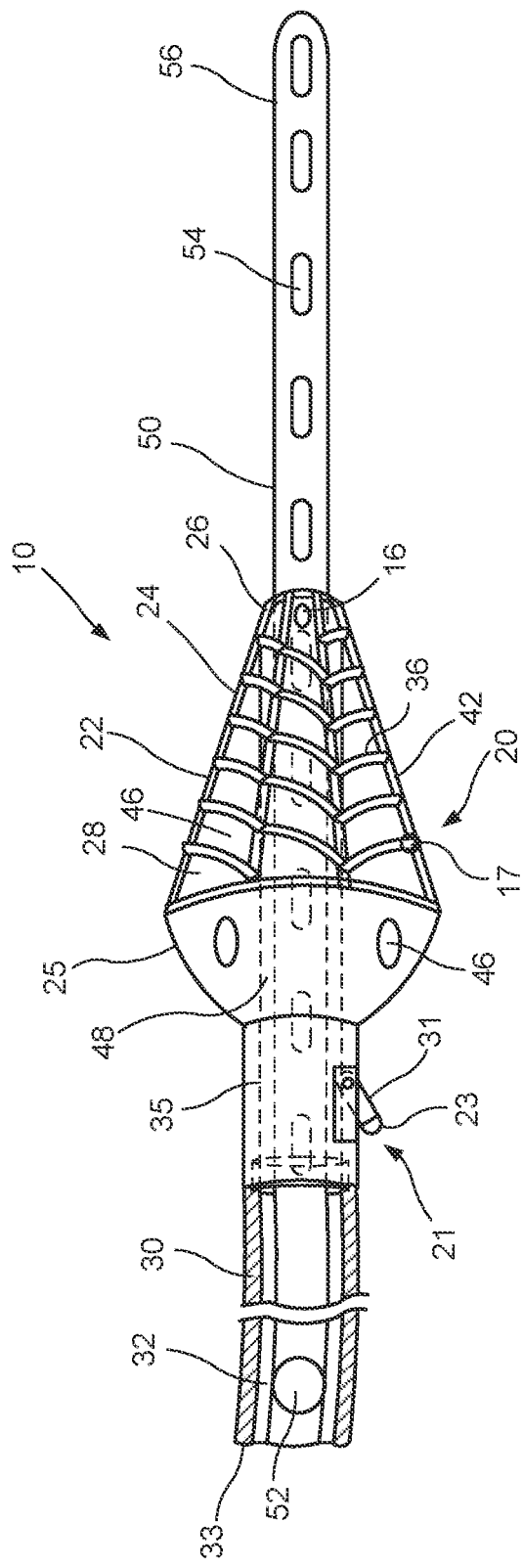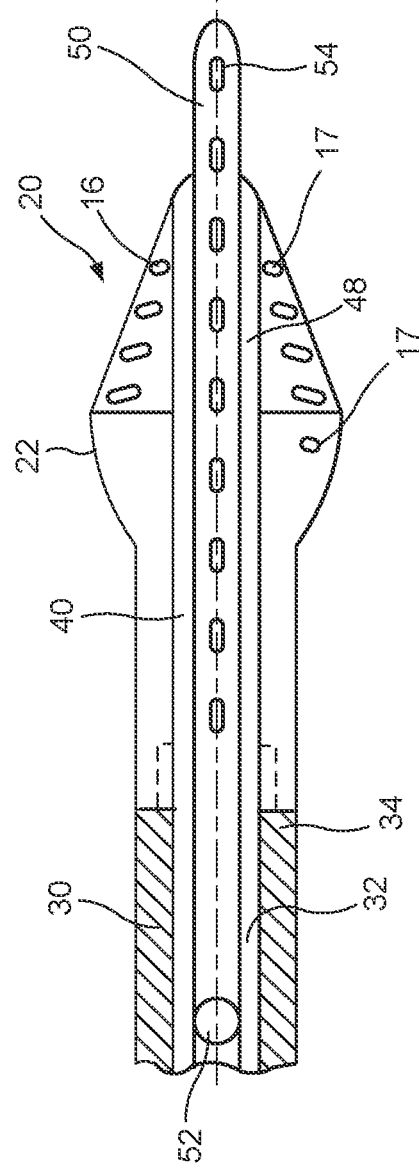
FIG. 1A
FIG. 1B

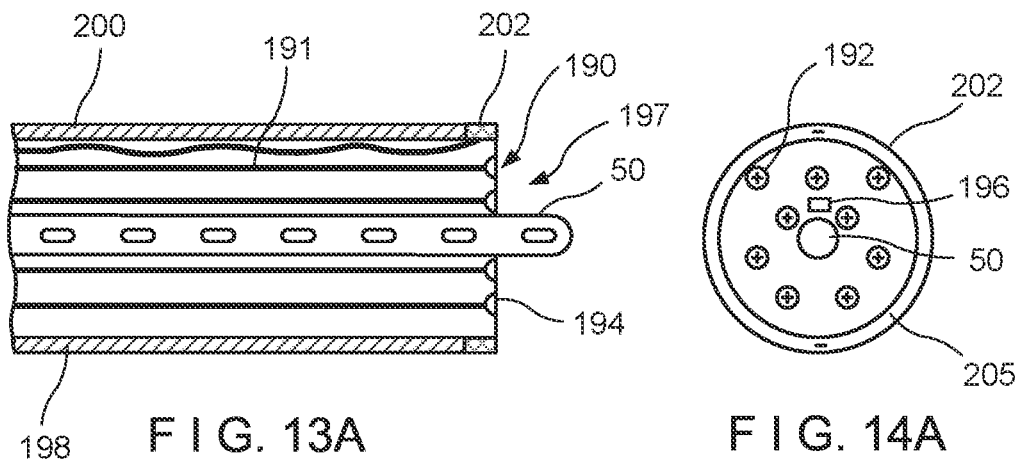
FIG. 13A
FIG. 14A
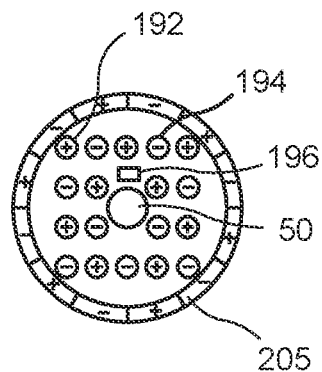
FIG. 14B
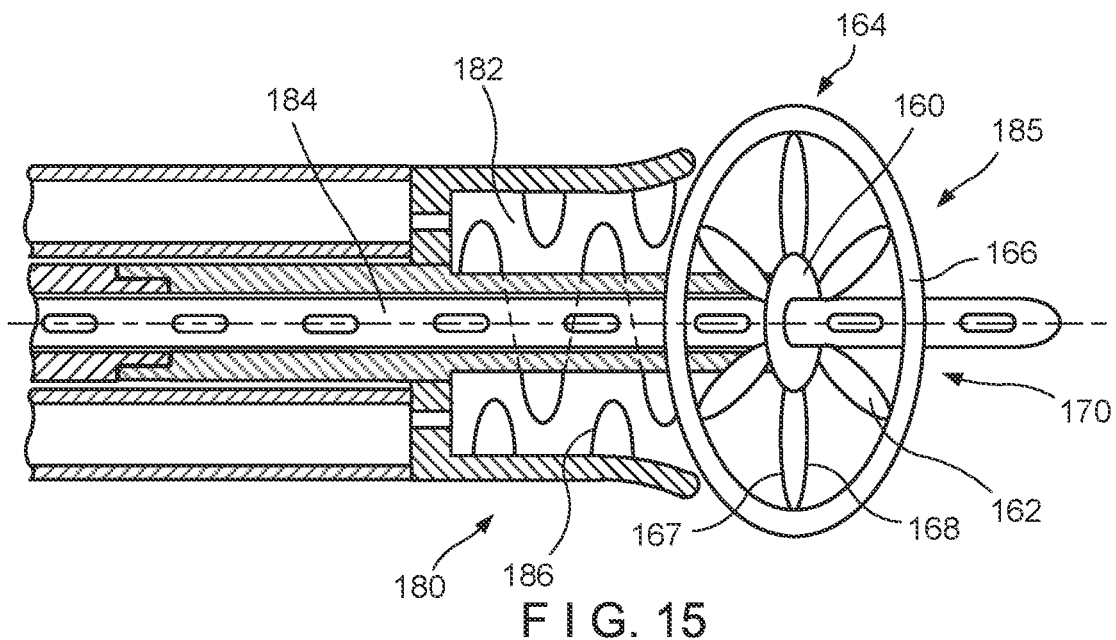
FIG. 15

DEVICES AND METHODS FOR INTRABODY SURGERY

CROSS-REFERENCE TO RELATED APPLICATION

The present application is a Divisional Application of currently pending patent application Ser. No. 16/406,683 filed May 8, 2019, which is continuation-in-part Application of patent application Ser. No. 16/192,781 filed Nov. 15, 2018 which claims priority of Provisional Patent Application Ser. No. 62/586,654 filed by the Applicant on Nov. 15, 2017 and Provisional Patent Application Ser. No. 62/680,260 filed by the Applicant on Jun. 4, 2018, the entire disclosure of these applications is hereby incorporated by reference.

FIELD OF THE INVENTION

The devices and methods of the invention generally relate to intrabody surgery and to treatment of occluded body lumens. In particular, the present devices and methods relate to removal of the occluding material from the blood vessels as well as other body lumens.

BACKGROUND OF THE INVENTION

The devices and methods of the invention are applicable for various types of intrabody surgery including, but not limited to cutting, breaking, coagulation, vaporization of any body tissue (including but limited to soft tissue includes tendons, ligaments, fascia, skin, fibrous tissues, fat, and synovial membranes, etc.; and muscles, nerves and blood vessels (which are not connective tissue) as well as hard tissue/bone and connective tissue, etc.) which involves reaching the targeted tissue through body channels including but not limited to blood vessels, ureter, oesophagus, stomach and duodenum (esophagogastroduodenoscopy), small intestine (enteroscopy), large intestine/colon (colonoscopy, sigmoidoscopy) or incision or cut through the body tissues (laparoscopic surgery) or similar.

Although devices and methods for removal of the occluding material from the blood vessels as well as other body lumens are discussed below in greater detail, it should be absolutely clear that this is one of many possible applications of the invention. In fact, devices and methods of the invention are applicable to many types of intrabody surgery, as identified above.

Cardiovascular diseases frequently arise from the accumulation of atheromatous material on the inner walls of vascular lumens, particularly arterial lumens of the coronary, peripheral and other vasculature, resulting in a condition known as atherosclerosis. Atheromatous and other intravascular deposits restrict blood flow and can cause ischemia which, in acute cases, can result in myocardial infarction or a heart attack, stroke or aneurysm. Atheromatous deposits can have widely varying properties, with some deposits being relatively soft and others being fibrous and/or calcified. In the latter case, the deposits are frequently referred to as plaque. Atherosclerosis occurs naturally as a result of aging but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Specific catheter-based interventions include angioplasty, atherectomy, RF ablation cutting devices, stenting, and the like. For the most part, however, this can be difficult or impossible in tortuous regions of the vasculature. Moreover, the catheters used for these interventions is often introduced over a guidewire, and the guidewire is placed across the lesion prior to catheter placement. Initial guidewire placement can be equally difficult if it needs to be placed through a long and multidirectional vasculature. This is especially so when the lesion occludes the blood vessel lumen to such an extent that the guidewire cannot be advanced across the lesion.

Occlusion in a blood vessel can be caused by a variety of materials from hard bone like calcium deposits to soft blood clot or piece of fatty deposit. Multiple type occlusions may be present in the same vessel. Currently different tools are used to remove different types of occlusion. Surgeons may need to remove one type of catheter and replace it with another one in order to work with different occlusion types. This extends treatment time, substantially raises cost, and increase risk for a patient. The inventions provide a more optimal and complete solution to this problem which include means to analyze the type of occlusion material present and then adapt the function of the occlusion removal device accordingly. Furthermore, the invention provides a combinational arrangement which enables sergeants to successfully work with different occlusion types without the need to remove one type of catheter/cutting tool and replace it with another one.

In prior art, there are known rotational atherectomy systems utilizing diamond drill tips/burrs to sand hard calcified occlusions to very small particles. While there are some discussions that the particles produced from 20 μm diamond-tipped burr that ablates plaque into micro-particles are smaller in size (~5 μm) than a red blood cell (8 μm), it is also known that larger particles of debris, produced when occlusion is being broken, are generated. Such larger particles can block blood capillaries and cause serious side effects. However, even when the occlusion particles are as small as blood cells, their presence in the blood stream may present a potential risk. Especially if such particles are accumulated at the essential body tissues, causing malfunctioning of the vital body organs. Visible accumulation of even smaller particles, for example tattoo ink particles (less than 1 μm [9]), is well known. The tattoos particles accumulation (tattoo) is well known to be permanent or at least long term. Since the tattoo ink is inserted into the skin, it mostly stays in the dermis. Thus, impact of the ink particles on other tissue and organs is localized. On the other hand, since the particles generated during the occlusion destruction can be carried out through the blood stream to the vital body organs, proper management of such become important. Some of the rotational atherectomy catheters have built-in arrangements with active aspiration to remove debris from the blood stream and evacuate the debris through the catheter or catch them into a separately inserted catch-basket downstream the blood vessel post occlusion zone. However, these aspiration (debris evacuation) arrangements are not optimally designed to remove all or most of such debris particles. The inventions propose more optimal and complete solutions to this problem.

The prior art solutions for removal of calcium plaque are often provided with forwardly shaped rotational drills. Such design presents a risk of accidental perforation of the blood vessel walls if such drill is pushed against the wall during the procedure. One of the aspects of the invention provides ways to limit such risks of vessel wall perforation as well as minimizes negative aspects of the procedure on any adjacent tissue.

The prior art is known for drill with the center of mass off center of the axis of burr rotation. This creates the centrifugal force which allows the burr to drill a wider opening in the lumen. However, it also leads to potential injuring of the vessel walls. This is because operator cannot control the application of centrifugal force which is constantly present in prior art devices. Injuring the blood vessel walls during atherectomy surgery is one of the leading causes of post atherectomy procedure restenosis-soft tissue growth from the vessel walls that closes the vessel lumen with soft occlusion.

The present invention offers a solution to prevent unwanted damage to the vessel walls by creating mechanism allowing an operator to remotely alter the position of the burr's center of mass as needed for the specific surgery site requirements.

In prior art, there are known rotational atherectomy systems utilizing diamond drill tips/burrs to sand hard calcified occlusions to very small particles. However, such drills are not suitable or effective in removing soft occlusions. The present invention offers solutions allowing use of mechanical drills to safely and effectively cut and remove both hard and soft occlusions in the vessels including in-stent restenosis ISR growth. The device of the invention is acceptable in orthopedic and other types of body surgery.

SUMMARY OF THE INVENTION

One aspect of the invention provides a device for intrabody surgery which includes a cutting arrangement rotatable by a hollow driveshaft, formed by a hollow front cutting region and a rear region. The front region is formed by multiple longitudinal drilling sections interconnected by transversely oriented cutting blade sections. The drilling sections are positioned at an angle to each other defining in combination with the cutting blades a conically shaped grid formation having a hollow internal cavity, with a plurality of ports between the drilling sections and the blades. A low-pressure zone is developed within the hollow internal cavity, wherein cut occlusion materials are aspired by the low-pressure zone through the plurality of ports into the hollow internal cavity for further evacuation from the cutting arrangement.

Another aspect of the invention provides a surgical device having a cutting arrangement for intravascular surgery rotatable by a driveshaft. The cutting arrangement formed by a substantially hollow front cutting region and a rear region, a connecting element extending from the rear region for connection to a distal end of the drive shaft, a sleeve is formed by a wall having a front edge and defining an interior hollow space. The sleeve is arranged at the connecting element and is movable between an expanded and contracted positions. In the contracted position the wall of the sleeve is interposed between the cutting region and a blood vessel wall. In the expanded position the front end of the sleeve engages an occlusion and allows the cutting region rotatable by drive shaft to engage with the targeted occlusion through the interior space of the sleeve. The sleeve is moved from the locked contracted position to the expandable position when rotational motion of the driveshaft and the cutting arrangement are initiated.

A further aspect of the invention provides system for intravascular surgery. The system comprises a hollow catheter, a cutting arrangement is provided at the proximal end of the catheter, a power source energizing the cutting device, a vacuum source disposed at the distal end of the catheter to create a low pressure zone within the hollow interior of the catheter and the cutting arrangement. A control unit is provided to adjust characteristics of the catheter and/or cutting arrangement based on the inputs obtained from a plurality of sensors provided within the cutting arrangement and the catheter. In response to the signals the control unit adjusts said characteristics depending on composition of the occlusion, physical properties of the catheter and cutting arrangement.

As to still another aspect of the invention a plurality of sensors is provided within the catheter and cutting arrangement to emit and receive various signals (optical, electromagnetic, acoustical, capacitance measuring) capable of detecting a composition of the occlusion, and to allow the control unit to generate controlling signals controlling operation of the cutting arrangement.

Yet another aspect of the invention provides catheter assembly in combination with a radiofrequency (RF) electrosurgical instrument.

The catheter arrangement includes a catheter body having hollow interior. A vacuum source is disposed at a distal end of the catheter to create a low-pressure zone. Multiple active electrodes are disposed a front end of the distal portion of the body for transmitting electrical signals and produce electrosurgical effects adjacent to the active electrodes for tissue cutting. Multiple passive electrode is disposed at the front end of the distal portion in closely spaced relationship relative to the active electrodes. Each passive electrode includes a passive tissue contact surface having an area greater than that of an active tissue contact surface of said corresponding active electrodes, said active electrodes. The electrodes are spaced from inner walls of said substantially hollow interior, openings provided to aspirate debris of ablation into and through the hollow interior of the body by the low-pressure zone.

BRIEF DESCRIPTION OF THE DRAWINGS

In the following drawings, the same parts in the various views are afforded the same reference designators. Referring now to the drawings which are provided to illustrate and not to limit the invention, wherein:

FIG. 1A is a diagram illustrating a burr according to one embodiment of the invention;

FIG. 1B is a partially sectional diagram of the FIG. 1A;

FIGS. 13A, 14A and 14B are diagrams illustrating a modified embodiment of the invention utilizing RF energy;

FIG. 15 illustrates a modified embodiment shown in FIG. 8 utilizing a rotatable blade assembly;

FIGS. 16A, 16B and 61C illustrate an embodiment of the invention utilizing a stiffening mandrel;

DETAILED DESCRIPTION OF THE INVENTION

Figure 1C:
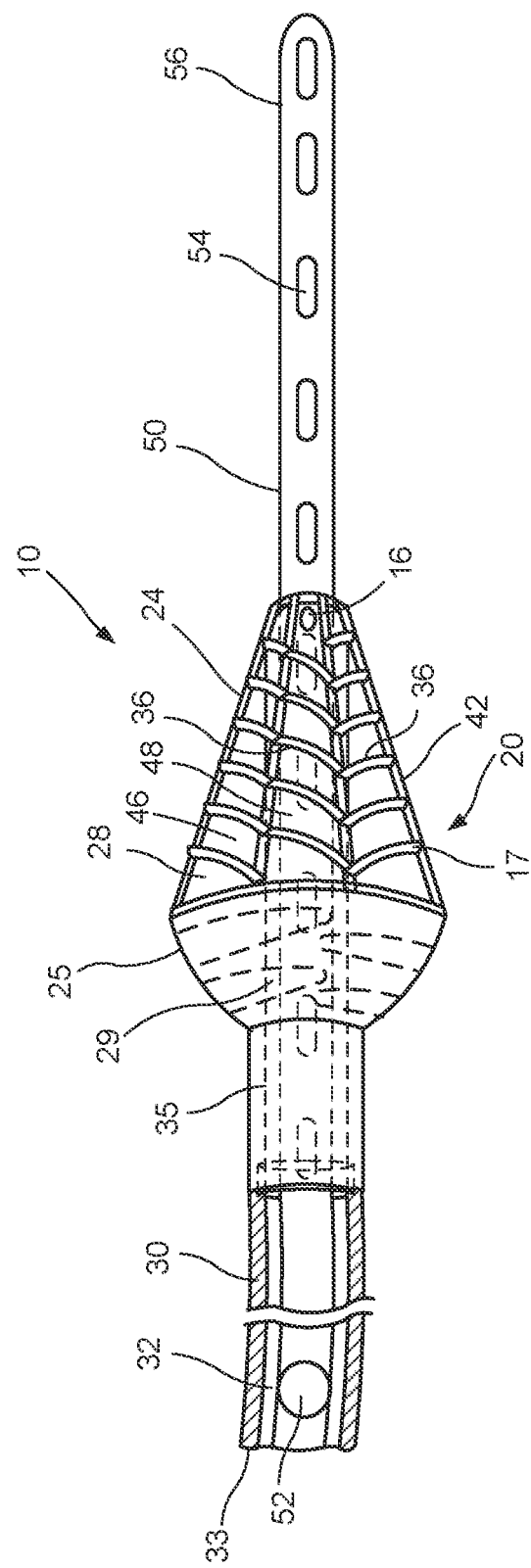
FIG. 1C is a diagram illustrating an alternate embodiment of the burr shown in FIG. 1A.

As used herein in the description of various components, "proximal" refers to a direction toward the system controls and the operator, and "distal" refers to the direction away from the system controls and the operator and toward a terminal end of the cutter assembly.

In general, the material removal system of the present invention comprises a control unit attached to one end of a catheter assembly and an axially translatable, rotatable drive shaft, with a cutter assembly positioned at the distal end of the drive shaft at least partially supported by the guidewire. The material removal system of the invention further comprises multiple sensors positioned at the cutter assembly area and along the length of the catheter. In one embodiment the system includes wires associated with sensors as well as with delivery of electric power to ultrasound or RF emitters.

The cutter assembly is translated over a guidewire to the material removal site and is actuated at the material removal site to cut, grind or ablate, or otherwise remove, the occlusive material. The control unit, and manifold assembly remain outside the body during a material removal operation.

We are referring now to FIGS. 1A and 1B illustrating a catheter assembly 10 of one embodiment of the invention provided for passing a high-rotational-speed burr/cutter 20 into blood vessels as well as to other bodily cavities and adapted to ablate and remove abnormal occlusions and deposits. The, burr/cutter 20 actuated by a driveshaft 30 and guided through the vessel to the application area by the guidewire 50, drills and cuts away the occlusions in the blood vessel.

The flexible guidewire 50 is navigated through one or more lumens such as blood vessels, to a desired material removal site. The catheter assembly 10 generally houses the burr/cutter 20, drive shaft 30, which also defines a lumen 32 which is used among other purposes for the aspiration and/or infusion of fluids. The catheter assembly 10 may be fixed to and advanced in concert with the drive shaft 30 to actuate a cutter assembly. The guidewire 50 and the catheter assembly 10 are introduced into a lumen of a patient and navigated or guided to the site of the desired material removal operation.

A proximal end 33 of the drive shaft is operably connected to vacuum or infusion pumps, while a distal end 34 of the drive shaft is operably connected to cutter/burr 20. Drive shaft 30 is preferably a flexible, hollow, helical, torque-transmitting shaft.

The burr/cutter 20 is formed having teardrop-shaped head 22 with a substantially hollow front cutting exterior region 28 and a substantially solid rear region 25. The front region 28 facing the occlusions formed by longitudinal drilling sections 24 extending along longitudinal axis of the cutter interconnected by transversely oriented cutting blade sections 36. The drilling sections 24 are positioned at an angle to each other defining in combination with the transverse cutting blades 36 a conically shaped grid formation culminating at a front tip 26 of the head 22. An internal hollow cavity 48 is formed inside of the grid formation with a central bore 40 passing through the rear region 25 and a connecting element 35. The grid formation defines a plurality of ports 46 between the drilling sections 24 and the blades 36. The central bore 40 and the internal cavity 48 extend longitudinally passing through the central part of the burr/cutter body and are adapted to movably receive the guidewire 50. The cutter/burr 20 is mounted at the distal end 34 of a flexible drive shaft 30 which transmits torque from a torque-generating device (not shown), such as an electric or pneumatic motor. The drive shaft 30 is guided by and surrounds a substantial portion of the hollow guidewire 50. It will be discussed in the application that the ports 46 provide passage of debris from the exterior of cutter/burr to the central bore 40 and the internal cavity 48. Optionally, ports 46 can be also provided in the rear region 25. The connecting element 35 extends from the rear region 25 of the burr in the proximal direction for connection to the distal end 34 of the drive shaft. In one embodiment the connecting element 35 has a cylindrical shape. On the other hand, any conventional configurations of the connecting element 35 are within the scope of the invention. As discussed later in the application, optionally a stop member 37 (see FIGS. 6 and 7) can be provided at the proximal end of the connecting element 35.

A plurality of ports 46 connects the exterior surface of the burr with its internal cavity 48 connected to the a lumen 32 and providing for aspiration of the debris created from drilling of the hard occlusion or cutting of the soft occlusion material. As illustrated in FIG. 1A, a central bore 40 passes through the burr/cutter to the internal cavity 48. The bore 40 is larger than an outer diameter of the guidewire 50, so that drive shaft 30 with the cutter 20 are slidable and easily translatable over guidewire 50. The longitudinal drilling sections 24 and cutting blades 36 are formed with sharp edges defining outer cutting surfaces. Cutting blades 36 and longitudinal drilling sections 24 may have sharpened edges to provide cutting and ablation. The longitudinal drilling sections 24 and cutting edges are arranged to direct debris produced during the cutting operation into the interior of the head 20 through the multiple ports 46. Longitudinal drilling sections 24 and cutting blades 36 may, additionally or alternatively, have an abrasive or cutting material bonded to one or more surfaces of longitudinal drilling sections 24 Material such as diamond grit is an example of suitable abrasive.

In one embodiment of the invention the cutting blades 36 are arranged in a radially symmetrical configuration. In another embodiment the cutting blades are asymmetrically arranged regarding a longitudinal axis of the head 22.

In the preferred embodiment ports/openings 46 are formed within the front region 28 of the cutter/burr, to provide communication with the internal cavity 48. More specifically, the ports 46 provide communication between the cutting front region 28 engaging the occlusion with the internal cavity 48 and also provide communication with the apertures 54 of the guide wire 50 disposed within the cavity 48.

Particles resulted from operation of the burr/cutter 20 are properly removed to prevent penetration into a blood stream. Debry particles resulted from use of the burr/cutter 20 are drawn through the ports 46 into internal cavity 48 by low pressure zone created in internal cavity by a vacuum pump connected to the distal end 34 of the drive shaft. The ports 46 also allow debris produced during the operation of the burr 20 to be aspired into the ports 54 in the guide wire. It will be discussed in greater detail below that the guide wire 50 made as a hollow tubular structure is also used as a suction/aspiration conduit for aspiration of occlusion debris, as the burr/cutter 20 drills away the occlusion. As discussed above, in the alternate embodiment, the ports 46 can be also provided within the rear portion 25 of the burr. The guide wire can be removed after the burr/cutter 20 is guided within the body lumen to the occlusion. Thus, the entire internal cavity 48 of the burr and the lumen 32 of the shaft can be used for aspiration purposes.

The front region 28 of the cuter facing the occlusion may have coatings on its inside or outside for various purposes, for example, for protection against corrosion by body fluids or for insulation against the high energy emitted towards its distal region. It can be of any dimension convenient for its intended use.

Additional structures at the front region 28 may help to prevent clogging of the suction conduit. For example, a filter, a screen, a mesh, a shield or other barriers can be provided at the distal region of the suction conduit.

Figure 8:
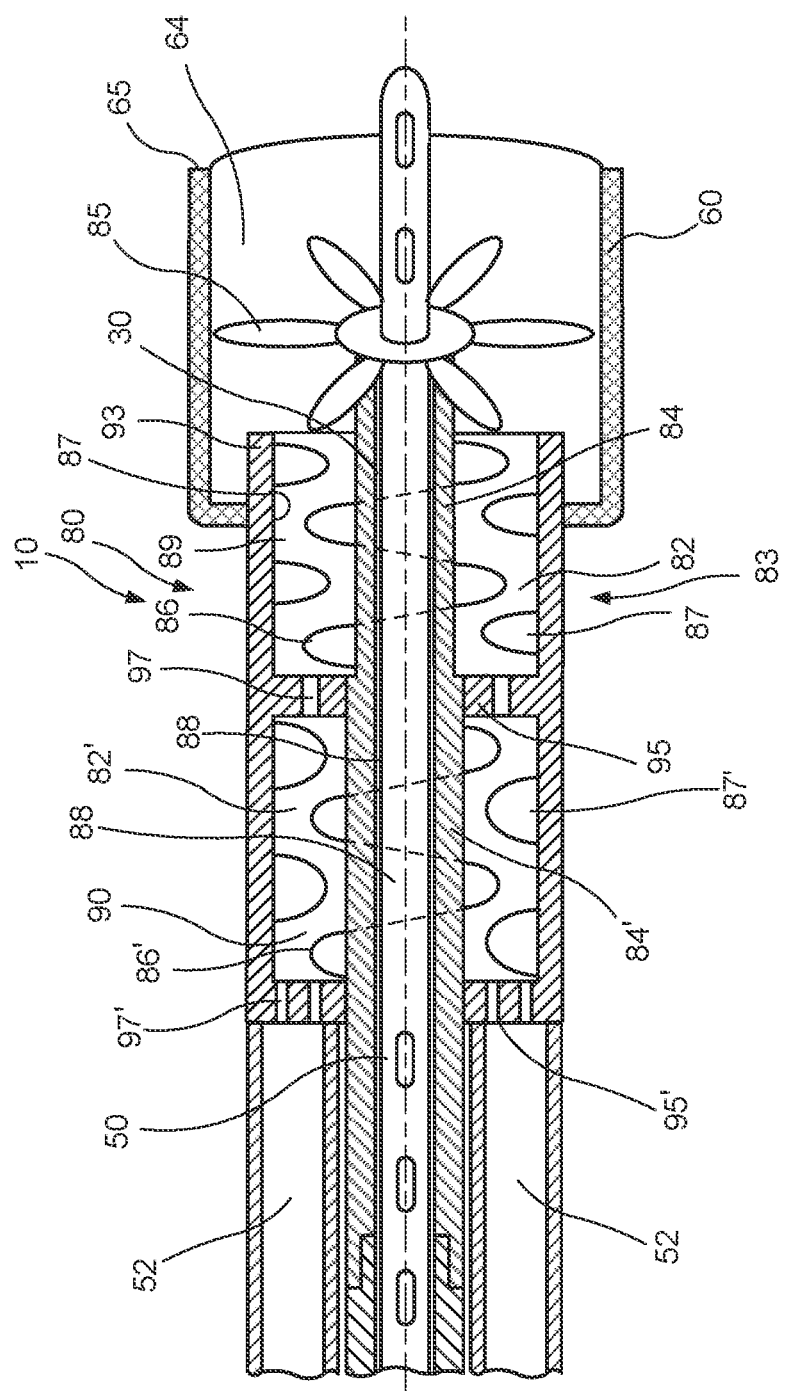
FIG. 8 illustrates another embodiment of the invention.

In an alternate embodiment, as illustrated in FIG. 1C an interior of the rear region 25 is substantially hollow. A plurality of knifes 29 is provided at an inner surface of the rear region 25 to further process occlusion materials accumulated within the inner cavity 48. More specifically, the knifes cut further and transport the materials along the chamber to the hollow interior of the drive shaft. In an alternate embodiment a processing unit, similar to the unit 80 illustrated in FIGS. 8 and 15 is formed in the hollow interior of the rear region 25. Such processing unit comprises a chamber having a drive shaft assembly with a conveying member rotationally positioned thereinside. The conveying member receives the occlusion material from the inner cavity 48, cuts it further and transports the material along the chamber to the hollow interior of the drive shaft.

In one embodiment of the invention the guidewire 50 is formed as a hollow tube. The drive shaft 30 is also hollow. The particle-entrained blood can flow from the burr 20 through the ports 46 into the interior cavity 48 and bore 40 and facing the guide wire 50 which is, at least partially, disposed within the hollow lumen 32 of the drive shaft connected to a suction or injection devices.

The hollow tube or central passage 52 of the guide wire 50 is used as a conduit for aspiration of occlusion debris. As illustrated, the guidewire 50 includes a plurality of apertures 54 along its distal end 56. Use of such hollow guide wire enables a clinician to catch occlusion debris more efficiently. This is because, the apertures 54 allow to catch/collect debris right at the site, where they are produced in the surgical procedure and before being disbursed. The hollow guidewire 50 can be made from metal, or plastic, or grafine or any other material which meets requirement for guide wire and is not permutable for liquid that contains debris of occlusion or embolus.

The hollow/tubular guidewire 50 if needed, is also capable of delivering fluid/medication/coolant to a target location. With apertures 54 liquid/fluid/medication is allowed to leak from the hollow passage 52 out into the vasculature passageway. The location of discharge of liquid/medication/coolant from the tubular guide wire 50 can be controlled by controlling size of the apertures 54 as well as the location thereof.

Further important functionality of the apertures 54 of the hollow guidewire 50 will become applicable when used in combination with the ports 46.

As to the aspiration aspect of the invention, a vacuum pump 70 (see FIG. 2) creates a low-pressure zone at the proximal end 33 of the drive shaft and the hollow guidewire to aspirate debris of the occlusion or embolus in the blood vessel or body lumen produced by the device of the invention.

Controllable entry of the cutter/burr 20 into calcified occlusions/obstructive lesion has to be assured for its predictable advancement. Thus, to facilitate such cutter advancement, the drive shaft 30 should be axially translatable with respect to guide wire 50. In the current prior art practice evacuation of residual debris is often complicated and time-consuming technique/procedure. In current practice tools similar to the burr/cutter 20 are nudged into a calcified occlusions area during rotation and then retracted. This manipulation in the prior art procedure permits evacuation of residual debris and to reestablish local circulation before making another cutting cycle on the lesion. On the other hand, in the present invention the ports 46 of the burr/cutter 20 establish a reliable communication between the burr cutting blades 36, the hollow passage 52, and the apertures 54 of the guidewire. In this manner residual debris are evacuated continuously during the procedure without the need for the complicated manipulations discussed above. Further, in the prior art arrangements for catching occlusion debris are often located behind cutting burrs (either opening into debris collecting sheath or a debris catching basket). This approach leaves a high probability that some of debris can escape into vasculature of a patient. In present invention the debris are collected at an immediate area, where the derbies are accumulated due to the negative pressure suction through the multiple ports 46.

Although the cutter/burr 20 has been discussed above for the removal of the occluding material from the blood vessels, it should be noted that application of the burr to many types of the intrabody surgery (as identified above) also forms a part of the invention. For example, in the ureteroscopy procedure, which treats and removes stones in the kidneys and ureters, the burr 20 may be used in combination with the respective flexible scope. In the procedure doctor passes the scope with the burr through patient bladder and ureter into kidney. Use of the burr 20 may be especially applicable for larger stone removal and can be combined with other techniques and/or tools including energy-based devices to break stones up. Use of the burr 20 may be also applicable in the ureteroscopy for the removal of polyps, tumors or abnormal tissue from a urinary tract. Further application of the burr 20 is in percutaneous nephrolithotomy or percutaneous nephrolithotripsy, combined with a small tube to reach the stone, the burr grinds/breaks the stone up. This action can be combined with the use of high-frequency sound waves, radio frequency or other energy-based devices. After the procedure the pieces of a stone are vacuumed up and removed from the system with a suction arrangement of the invention.

FIG. 1A also illustrates an optional feature of the burr/cutter 20, wherein a center of the mass is not located in the center of the burr rotation, so as to create an orbital effect. More specifically the feature provides a mechanism 21 that moves the center of the mass away from the center of the burr rotation providing an operator with another controlling function. Thus, the center of mass is moved away from center of the burr rotation when operator wishes to drill a wider opening in the occlusion. On the other hand, the center of mass of the burr remains in the rotational center during other periods of surgery, thus preventing injuring to the blood vessel walls by the uncontrollable rotational forces that press the burr ablative surfaces to the vessel walls. As illustrated in FIG. 1A, the mechanism 23 consists of multiple or at least two weights initially located symmetrically relatively to the axis of the burr rotation, with one of the weights 23 being moved away from the rotational center. A pivoting arm 31 with the weight 23 pivots away from the connecting portion 35 when it is released by the operator. In the mechanism release and movement of the arm can be controlled in any conventional manner, mechanically, electrically, wirelessly, etc.

Figure 18A:
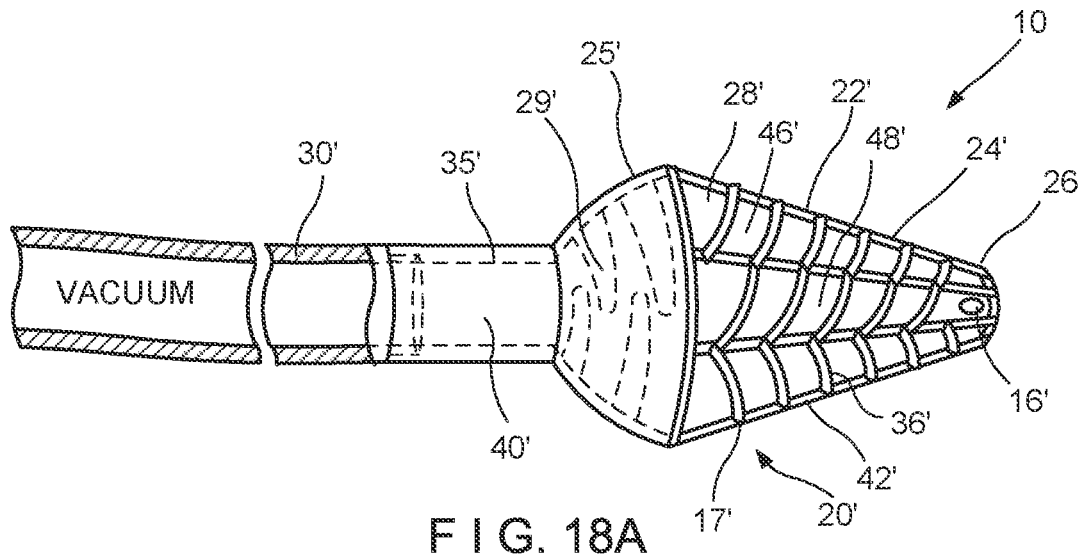
FIGS. 18A, 18B and 18C illustrate surgical tools according to a further embodiment of the invention.
Figure 18B:
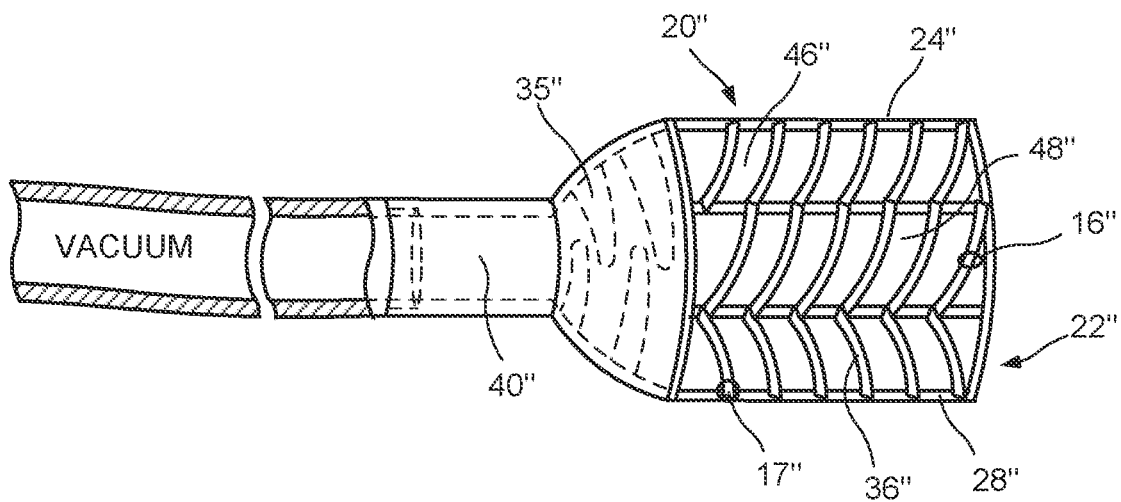
Figure 18C:
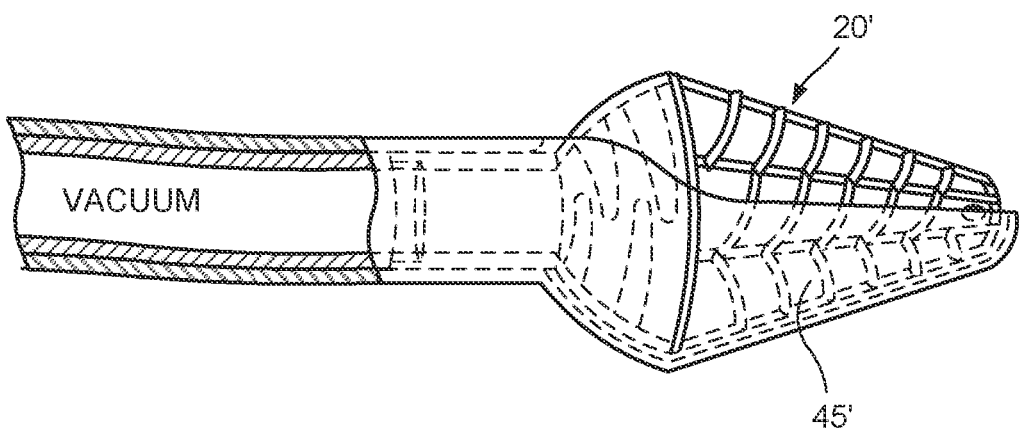

We are referring now to FIGS. 18A, 18B and 18C illustrating further embodiments the burr/cutter of the invention provided for use in orthopedic and other types of surgery. Application of these surgical tools includes, but is not limited to drilling of the bones and surface ablation, scrubbing or scraping of bones, ligaments, meniscus, cartilage etc. The bur/cutter 20' of FIG. 18A is formed having conical head 22' with a substantially hollow front cutting exterior region 28' and a substantially solid rear region 25'. The front region 28' facing operation site is formed by longitudinal drilling sections 24' extending along longitudinal axis of the cutter interconnected by transversely oriented cutting blade sections 36. The drilling sections 24' are positioned at an angle to each other defining in combination with the transverse cutting blades 36 a conically shaped grid formation culminating at a front tip 26' of the head. The grid formation defines a plurality of ports 46' between the drilling sections 24' and the blades 36'. The ports 46' provide passage of debris from the exterior of cutter/burr to the internal cavity 48'. As discussed above, conically shaped surfaces of the burr/cutter 20' are used for to drilling, surface ablation of the bones, etc. The bur/cutter 20' of FIG. 18C is similar to that of FIG. 18A, but is also provided with an exterior shield/cover 45" preventing the materials/particles developed during the surgery from being dispersed, so as to be directed into the interior cavity 48' for evacuation from the device by suction. The bur/cutter 20" of FIG. 18b is formed having cylindrically-shaped head 22" with a substantially hollow front cutting exterior region 28" and a substantially solid rear region 25". The front region 28" is formed by substantial straight drilling sections 24" interconnected by transversely oriented cutting blade sections 36". The drilling sections 24" define in combination with the transverse cutting blades 36" a cylindrically shaped grid formation with a plurality of ports 46". Optionally, a plurality of knifes 29" can be provided at an inner surface of a hollow rear region 25" to further process occlusion materials accumulated within the inner cavity 48".

Figure 2:
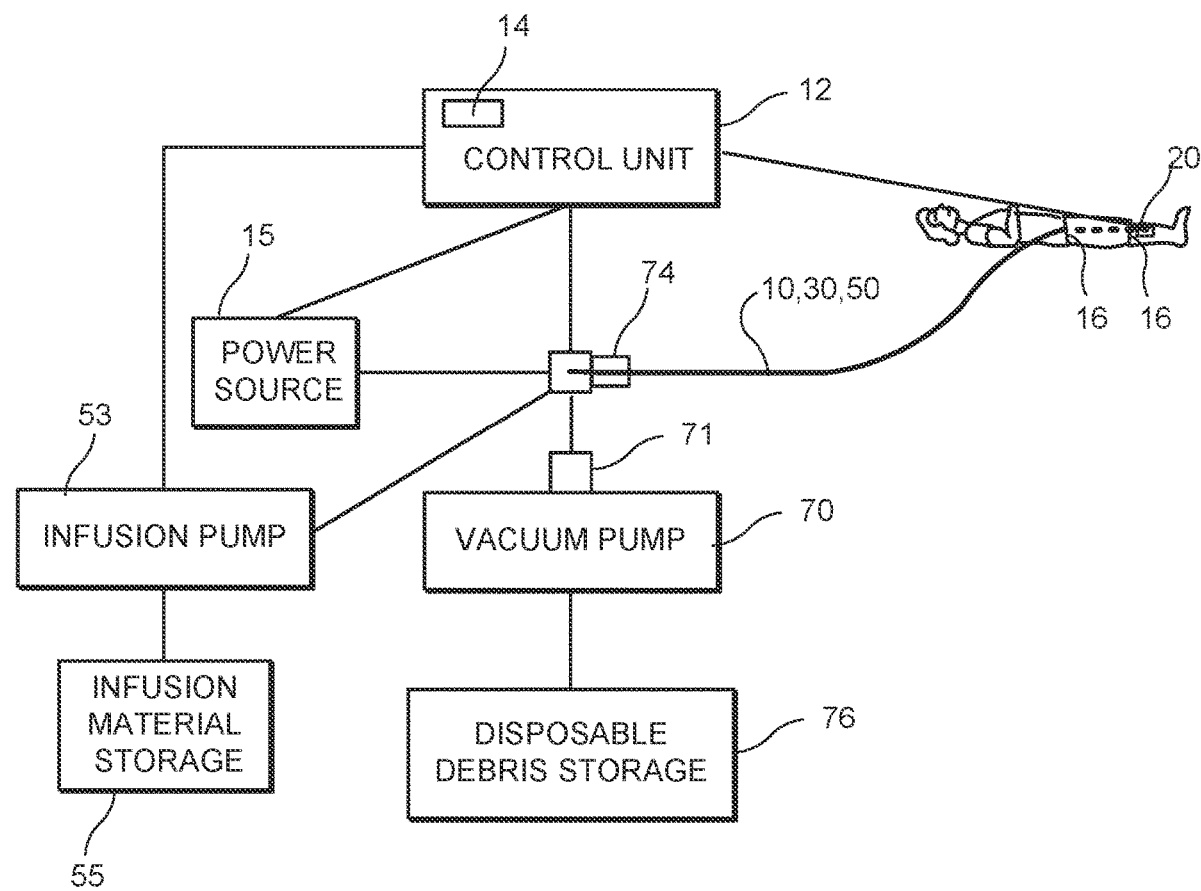
FIG. 2 is a diagram illustrating the system of the invention.

As illustrated in FIG. 2 the control unit 12 houses a programmable logic controller 14 or microchip and power source 15 in operable communication to provide power and to control operation of various units of the system of the invention. The control unit 12 preferably comprises a base arranged so that the control unit may be stably supported on a work surface or a body surface during material removal operations. The control unit 12 also preferably incorporates control systems for actuating, adjusting and providing system information concerning power, drive shaft rpm, drive shaft axial translation, aspiration, infusion, which displays reading of sensors located on the catheter and cutting instrument and the like. The control unit may include, but not limited to vacuum control unit, cutter advancer unit, guidewire control unit, cutter assembly drive control, and aspiration and infusion control unit. The control unit 12 also controls a block providing information concerning operating conditions and feedback from the material removal site to the operator. By means of a computer or microchip 14 the control unit 12 utilizes inputs received from multiple sensors 16 located at the burr/cutter 20 and/or other critical regions of the catheter assembly to continuously updated output to an operator including such operating parameters as temperature at the material removal site; cutter assembly rotation rate and/or advance rate; aspiration rate and/or volume; infusion rate and/or volume; and the like. Control unit 12 may additionally provide adjustable controls permitting the operator to control operating parameters of the cutter assembly and material removal operation.

As illustrated in FIG. 2, the control unit 12 is provided to regulate the power source 15 for the optimum output level based on type and characteristics of the targeted occlusion (hard, soft, blood, etc.) and/or characteristics of the burr catheter (length, diameter, temperature, etc.). Characteristics of the control unit 12 may be adjusted by the operator or automatically based on inputs from the sensors 16. Controlling various characteristics/parameters at the operation cite are based on the information provided by sensors positioned at the distal end of the catheter and the burr, such as for example speed of rotation, temperature, etc. Such characteristics can be manually or automatically adjusted based on the signals and data received from the sensors 16 installed within the cutter/burr 20.

Sensors 16 may emit and receive various types of signals (optical, electromagnetic, acoustical, capacitance measuring) that will change parameters depending on the composition or other physical properties of the occlusion and/or tissue surrounding occlusion and/or physical characteristics of the catheter itself, so as to allow the control unit 12 to calculate and generate proper signals controlling operation/speed of rotation, etc. of the burr 20.

Sensors 16 located at the front portion 24 of the burr 20 are able to recognize (determine) the physical and chemical properties of the occlusion. A computer or microchip 14 associated with the control unit 12 receives and analyzes information/data obtained by the sensors 16 and generates signals to adjust parameters of the power source 15 to optimize the destruction of an occlusion in the blood vessel and/or to produce other desired effect on targeted tissue. As an example, the control unit 12 analyzes information/data obtained by the sensors 16 and generates signals to adjust parameters of the power source 15 to optimize rotational speed, etc. of the burr 20. This includes also applying different physical mechanisms of action to destroy occlusion. For example, the cutting arrangement can combine mechanical cutting tool and RF cutting electrodes which can be activated by the control unit 12 interchangeably based on the signal from the sensors describing the occlusion material characteristics which may require different tools for best removal.

The sensors 16 are capable of detecting the level of hardiness/calcification, water/moisture content, etc., within the material of an occlusion. As the burr 20 passes through various areas of the occlusion, optimal levels of rotational speed, etc. can be achieved for each zone of treatment. For example, a higher speed of rotation can be provided for the destruction of calcinated occlusion having higher degree of hardiness. On the other hand, lower speed will be generated for the areas with softer occlusion materials for more effective blade cutting action.

Utilization of the cutting burr 20 is also accompanied by automatic target feedback, thermal feedback for example, to precisely control the speed of rotation, etc. This is needed to prevent damage to surrounding tissue. For this purpose, non-contact thermal detectors 17 can be provided. The output of the non-contact, thermal detectors 17 can be used to adjust the output of the power source 15 to maintain selected characteristics including temperature at the treatment site.

In the invention to effectively control the destruction of the occlusion, a condition of the entire artery body and/or the tissue surrounding the operation site is monitored by the detector 17 adopted to detect irradiation reflected from such tissue. One of the essential functions of the detector 17 is to control the effect of the drilling/ablation on the tissue surrounding the site. In every individual case a doctor sets specific rotational, etc. characteristics to produce the required effect. If a situation at the operation site becomes unfavorable, for example the temperature exceeds predetermined limits, the detector 17 generates a signal directed to the control unit 80, which in turn produces a correcting signal to the power source 15 or to the control unit 12.

The computer or microchip 14 of the control unit 12 receives and analyzes the information obtained by the detector 17 and to generate a control signal to adjust parameters of the power source 15 in such a way as to optimize the destruction of an occlusion in the blood vessel or other desired effect on targeted soft tissue.

In an alternate embodiment the control signal generated by the thermal detector 17 energizes the cooling arrangement (see above) to directly or indirectly lower/adjust temperature at the site. This is necessary to exclude possibility of damaging an adjacent tissue. The detector 17 and the sensors 16 can be made utilizing a wide variety of photoelements, photoresistors, photodiodes and similar devices. Overheating may also occur in the length of the catheter particularly where the catheter is bended to sharp angle thus installing temperature sensors along the length of the catheter may improve safety profile of the device.

As discussed above, frictional forces resulted from the engagement/drilling between the burr 20 and the material of the occlusion, as well as other factors may result in temperature elevation of the surrounding tissue. In the invention, the temperature elevation occurs controllably without causing irreversible thermal damage to the surrounding tissue of the arteries. The control unit 12 adjusts the energy to maintain a pre-selected target temperature at the site. In one embodiment of the invention, to maximize patient safety, an optional continuous or pulsed cooling device can be provided to deliver a coolant from the infusion material storage 55 by means of the infusion pump 53 through the hollow guide wire 50 to the operation site during or after surgical procedure.

The diagram of FIG. 2 schematically depicts a system according to one embodiment of the present invention that may be connected to the cutter 20 to evacuate the ablated or cored bodily material from a subject's vascular system using various embodiments of the cutter/burr 20. The vacuum pump 70 provided at the proximal end 33 of the drive shaft creates low-pressure zone resulted in suction pressure within the lumen or hollow inner space 32 of the drive shaft and the passage 52 of the guide wire 50 to evacuate cut and/or ablated bodily material directly from the operating site in the vascular system.

In another embodiment, the vacuum pump 70 is interconnected to a pulse modulator 71, the actuation of which creates one or more pressure differentials to the aspiration system. Accordingly, by the use of the pulse modulator 71, rather than creating a constant suction pressure within the system to evacuate cut and/or ablated bodily material from a subject's vascular system, the aspiration system of the invention applies alternative pressure(s), thereby creating pulses of suction pressure within the lumen. Utilizing a series of constant and/or varying pressure pulses is potentially beneficial in aspirating bodily material, particularly when aspirating larger cylindrically looking core or plug like shapes of bodily material.

Aspirated liquid and/or particle from an area near distal end of the tool are accumulated and stored in the disposable debris storage 76. A filter 74 can be also provided upstream of system for filtering debris and aspirated bodily material and also for providing visual feedback to a user related to the type, quantity, and flow rate of material being removed from a patient. The debris container 76 may be in fluid communications with the vacuum pump 70 and may include one or more known devices for collecting and filtering materials removed from a patient. The container 76 may have transparent sidewalls for providing visual feedback to a user regarding flow-rate, content, coloration, etc. Those of skill in the art will appreciate that various types of collection containers may be used. The collection container 76 and/or filter 74 may also comprise one or more custom filter features with various mesh sizes, capacities, etc. based on the specific application.

The distal end 56 of the hollow guide wire 50 functioning as a suction conduit can be made of a variety of flexible or rigid materials or a combination of both, such as metal or plastics. Still further, the distal end 56 of the guide wire formed as a suction conduit can be made of a material different from the body of the hollow guidewire. For example, one might want to make the distal end 56 with a more heat-resistant material to withstand high energy directed to it. It may also be desirable to use a more impact-resistant material to withstand the initial impact from the solid particles drawn by the suction force.

Figure 3:
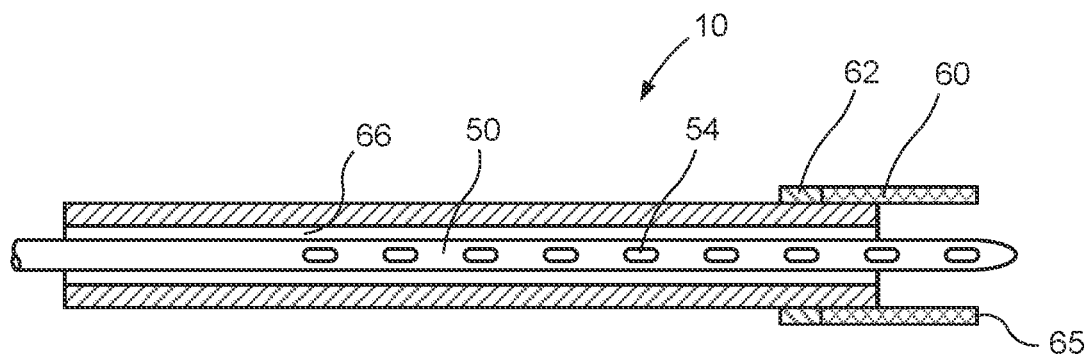
FIG. 3 illustrates a distal end of a catheter including a slidable sleeve in an extended position according to another embodiment of the invention.

Referring now to FIG. 3, showing an expanded/working position of a sleeve 60 provided for slidable motion along an exterior of the catheter according to another embodiment of the invention. The distal end of the catheter assembly 10 is provided with the sliding sleeve 60 having an activating mechanism 62 provided for controllable movement of the sleeve back and forth along the catheter exterior. In one embodiment of the invention the activating mechanism 62 is spring controlled. However, the activating mechanism 62 can be energized/actuated in any conventional manner, such as for example electrical, pneumatic, etc. mechanisms are contemplated. The front/distal end 65 of the sleeve 60 is designed to establish a tight contact with the occlusion. For example, the distal end 65 can made of a resilient material capable of adopting to evolving configuration of the external part of the occlusion during the procedure. Therefore, catching the occlusion debris and channeling them into the hollow tubular passage 66 for aspiration has been enhanced. As illustrated, in the working position the sleeve 60 extends outwardly from the exterior of the catheter 10. In this arrangement the diameter of the outer periphery at the distal end of the catheter is slightly increased. In the contracted position the sleeve 60 is positioned along the exterior surface of the catheter.

Figure 4:
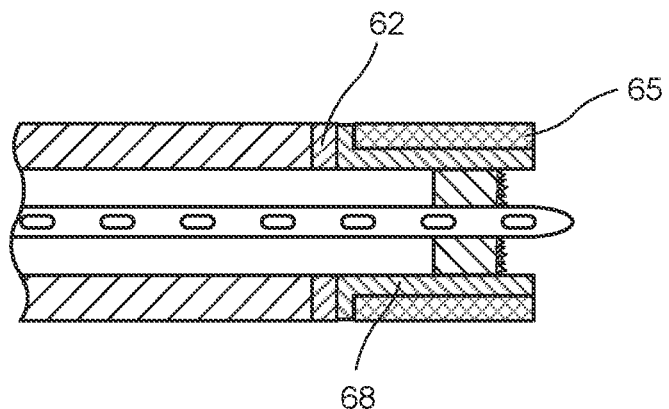
FIG. 4 illustrates the slidable sleeve in a retracted position.

In another embodiment, illustrated in FIG. 4, a circumferential recess 68 is formed within the distal end of the catheter body having the depth and length corresponding to the respective dimensions of the sleeve 60. The exterior surface of the sleeve is in flash with the exterior surface of the catheter. Prior to the catheter's placement through the blood vessel lumen to the operation site, the sleeve 60 is pressed inwardly in the direction of the proximal end to overcome resistance of the activating mechanism 62. As a result, the sleeve 60 is submerged within the circumferential recess 68. In this locked position the exterior of the sleeve 60 is in flash with the exterior of the catheter. Upon delivery and proper positioning at the site, the activating mechanism 62 is released-unlocked and the sleeve 60 is moved to the expanded working position to provide a tighter contact between the distal end 65 of the sleeve 60 and the occlusion.

Figure 5:
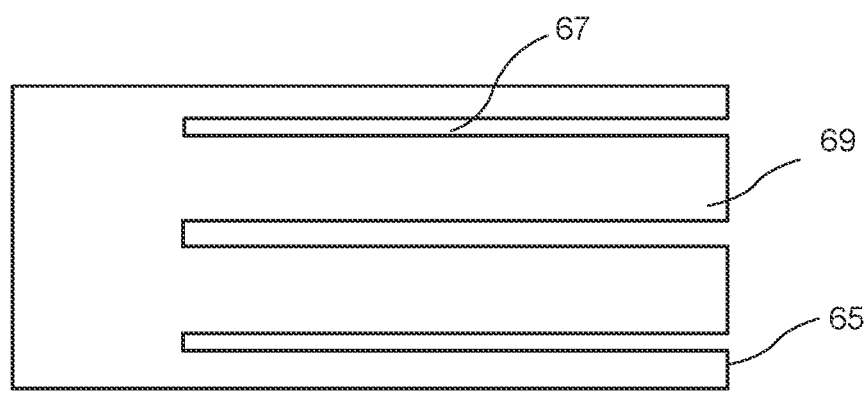
FIG. 5 illustrates another embodiment of the slidable sleeve.

Turning now to FIG. 5 showing an alternate embodiment, provide to further increase ability of the sleeve to accommodate randomly shaped occlusion for optimally sealing the cutting/drilling site. As illustrated in FIG. 5, longitudinal slits 67 are circumferentially arranged within the sleeve body forming a plurality of segments. The slits 67 extend inwardly from the distal end of the sleeve to separate the sleeve body into a plurality of segments 69. In one embodiment of the invention front area of the segments 69 can be curved and/or formed from a resilient material to further improve engagement with the occlusion. Any reasonable number and configuration of the slits and/or segments are within the scope of the invention.

Figure 11:
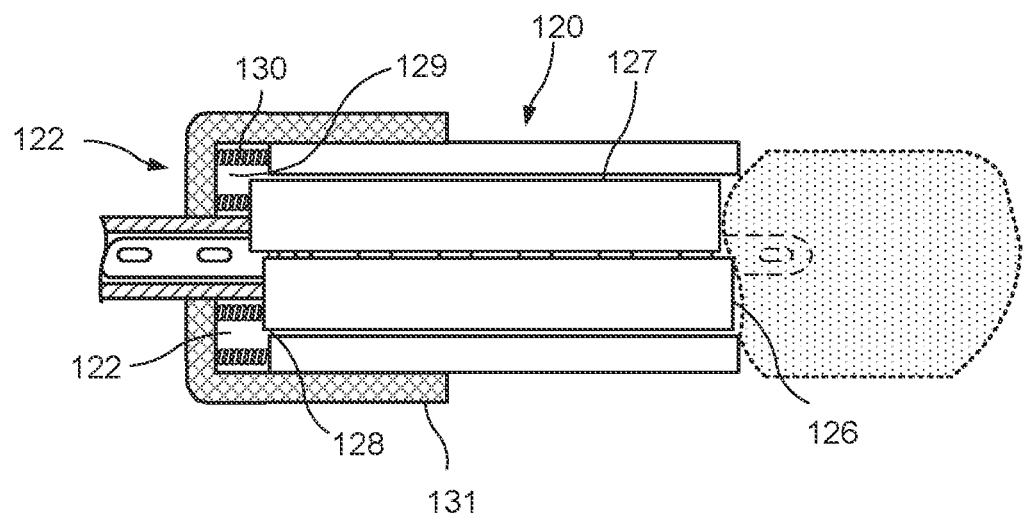
FIG. 11 is a view of a modified embodiment utilizing the slidable sleeve.
Figure 12:
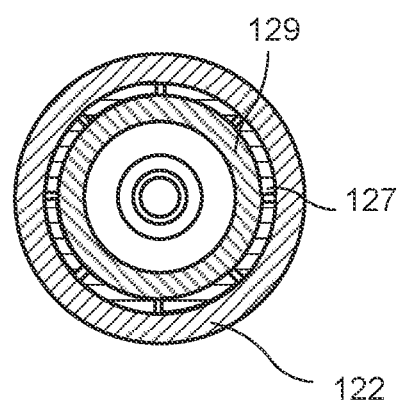
FIG. 12 is a section view of the embodiment shown in FIG. 11.

Turning now to FIGS. 11 and 12 showing another embodiment of a sleeve assembly 120 provided to further increase ability of the sleeve to augment randomly shaped occlusion for optimally sealing the cutting/drilling site to maximize catching debris of the destroyed occlusion. Longitudinal slits are circumferentially arranged within the sleeve body forming a plurality of segments. Such segments are able to longitudinally move independently each other to optimally adapt to the random shapes of possible occlusion deposits. The assembly 120 consists of an external base 122 formed by a cylindrical side wall 131 and a rear wall 124, so that a hollow inner cavity 129 is defined therebetween. A plurality of separated from each other engaging segments 127 are positioned in the inner cavity 129 for independent slidable movement along a longitudinal axis the assembly. Any reasonable number of the segments can be symmetrically arranged within the cavity. Each engaging segment consists of at least a front part 126 adapted for engagement with an occlusion and a rear part 128 adapted for movement within the inner cavity 129. A biasing member or a spring 130 is positioned between the rear part 128 of each segment and the rear wall 124 of the base. In use, upon the sleeve approaching the occlusion, the front parts of each segment which is pressed by the biasing member 130, engages the respective area of the occlusion having a specific configuration. This occurs independently from other segments. The front part 126 of each segment is formed to provide a tight contact with a respective area of the occlusion. In one embodiment, the front part 126 is made of a resilient material capable of adopting to evolving configuration of the respective part of the occlusion. Therefore, the sleeve assembly 120 provides an improved tighter contact between the front parts of the segments and the occlusion during the procedure.

Figure 6:
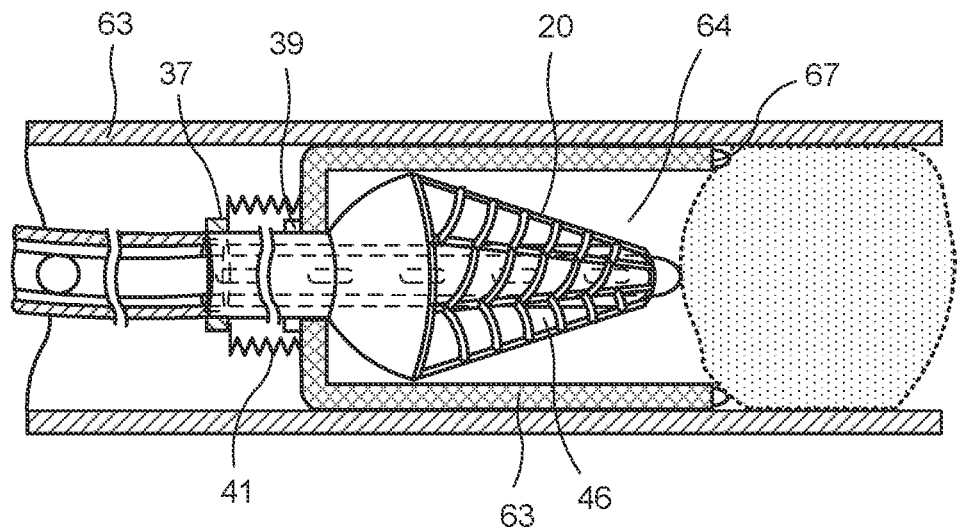
FIG. 6 is a diagram illustrating one position of an embodiment combining the burr and the slidable sleeve.
Figure 7:
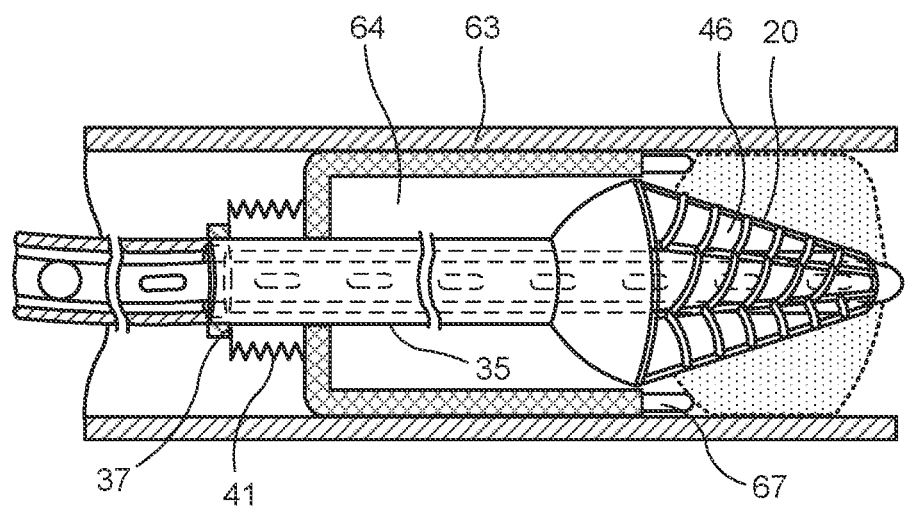
FIG. 7 is a diagram illustrating another position of the embodiment shown in FIG. 6.

FIGS. 6 and 7 illustrate yet another embodiment of the invention which combines application of the above-discussed burr/cutter 20 with the sliding sleeve 60 movably positioned at the connecting element 35 of the burr. The stop member 37 is provided at the proximal end of the connecting element 35. As illustrated, the sleeve 60 is arranged for a movement along the connecting element 35. The advancement of the sleeve in the proximal direction is limited by the stop 37. The hollow interior of the sleeve defines an interior space 64 which accommodates the burr 20 and serves as its housing. As illustrated in FIG. 6 in the initial position on the connecting element the burr 20 is positioned within the chamber 64, so that the wall of the sleeve extends over the burr exterior. This position of the sleeve is locked by a key 39. This arrangement allows for safe travel of the burr 20 covered by the sleeve 60 through a blood vessel to an occlusion area. When the burr covered by the sleeve reaches the occlusion, rotation of the burr by drive shaft is initiated. The torque moment at the beginning of the rotation breaks the key 39 causing disengagement of the burr and sleeve. Thus, independent operation of the bur and the sleeve is initiated. As illustrated in FIG. 7 rotating burr 20 drills the occlusion. On the other hand, the sleeve becomes independently slidable by means of the loaded spring arrangement 41 which pushes the sleeve 60 toward the occlusion to establish a contact therebetween, so as to further maximize catching of the cut debris into the internal hollow space 48 of the burr.

An abrasive or cutting material is bonded or by any other conventional means attached to the distal end 67 of the sleeve, forming an auxiliary cutting region. IN an alternate embodiment, a cutting element or a cutting edge can be formed at the distal end 67 instead of the abrasive material. In this manner this assembly is provided with two cutting regions, including the burr/cutter 20 and the auxiliary cutting region at the distal end 67.

To drill away the occlusion the rotating burr 20 is moved by the advancing catheter in the distal direction. After that rotation motion of the sleeve 60 is initiated. In this process a major central portion of the occlusion is cut or drilled away by the cutting burr 20. Furthermore, as illustrated in FIG. 7, a portion of the occlusion along inner walls of the blood vessel or lumen is removed or cut away by rotation of the auxiliary cutting region provided at the distal end 67 of the rotating sleeve. Thus, this arrangement enables a practitioner to eliminate or cut away the entire occlusion in one procedural step. In the prior art however, the portion of the occlusion disposed along the inner walls of the blood vessel or lumen is not removed due to relatively small outer diameter of the burr.

During the process of inserting the catheter through the blood vessels to the point of occlusion and during the cutting procedure, walls of the sleeve 60 isolate the burr 20 from the blood vessel walls 63. Thus, a risk of accidental perforation of the blood vessel walls 63 or any other adjacent tissue during the procedure is minimized. The interior space 64 of the sleeve creates a conduit which accommodates materials cut during the procedure and improves the flow of various fluids during aspiration and/or infusion.

Among essential functions of the sleeve assembly illustrated in FIGS. 6 and 7 is to form an enhanced engagement with the occlusion. Thus, that the distal end of the sleeve provides, upon engagement with occlusion an isolation of and a potential vacuum within the space 64, having the burr 20 being positioned thereinside. Upon rotational/drilling motion of the burr, created derbies or cut materials are accumulated/disposed within the inner space 64 and evacuated by suction through the plurality of ports 46 into the internal hollow space 48 of the burr. The invention also provides the burr-sleeve assembly of various sizes, so as to enable a practitioner to more precisely accommodate specifics or sizes of each vessel or lumen being operated upon. Thus, the larger size is accommodated by the sleeve 60 having a larger diameter, whereas smaller diameter sleeves are provided for smaller size vessels. This feature is especially important when a close contact between the exterior of the sleeve and interior of the vessel is needed for the removal of parts of the occlusion disposed adjacently to the vessel's interior surfaces. During the stage of inserting the catheter into the vessel and through its movement through vascularity to the surgery site (occlusion) the sleeve 60 is locked in such a way that it surrounds the burr/cutting surfaces thus protecting the internal walls of the blood vessels from being injured by the burr cutting surfaces and therefore minimizing risk of in vessel unwanted growth of soft tissue as a reaction to the wounds caused by such cutting surfaces being pushed through the vessels to the occlusion site. When burr/cutting arrangement reaches the occlusion site the sleeve 60 is released from the locked position with start of the shaft rotation.

It should be noted that application of the slidable sleeve 60 is not limited to the removal of the occluding material from the blood vessels. The sleeve 60 can be used in many types of the intrabody surgery (as identified above). For example, it can be used in ureteroscopy procedure, which treats and removes stones in the kidneys and ureters. The sleeve 60 may be used in combination with the flexible scope, which is passed through patient bladder and ureter to provide an enhanced contact with kidney. Use of the sleeve 60 facilitates larger stone removal, combined with RF cutting device, which passes through the scope to break stones up. Another example is use of the movable sleeve 60 in the ureteroscopy for the removal of polyps, tumors or abnormal tissue from a urinary tract in orthopedic or general surgery. Similar to the above discussed applications, the sleeve 60 can be used in percutaneous nephrolithotomy or percutaneous nephrolithotripsy, combined with a small tube to reach the stone and break stone up with high-frequency sound waves or RF cutting device. The broken pieces are vacuumed up and removed from the system by a suction arrangement of the invention.

Figure 14:
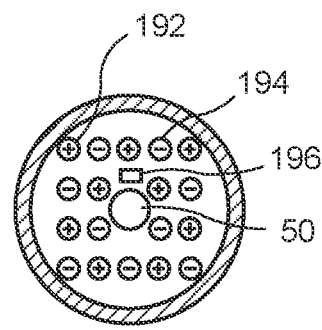

Although the assembly combining the burr/cutter 20 with the sliding sleeve 60 has been discussed above, it should be noted that use of the cutter/burr with other type of protective devices is within the scope of the invention. For example, an assembly where the burr/cutter 20 is combined with the sleeve arrangement illustrated in FIGS. 11, 12 and 14 is also contemplated.

In a further embodiment of the invention illustrated in FIG. 8, a processing unit 80 with a rotatable blade assembly or cutting element 85 is provided at the distal end of the drive shaft 30 to cut and macerate the occlusion (embolus) and to evacuate cut materials away from the site. The rotatable blade assembly 85 includes a hub and a plurality of blades arranged at the hub. Each blade is formed having a leading cutting edge and a trailing edge and extend in a plane generally perpendicular to the axis of rotation.

The processing unit 80 comprises a chamber 82 having a drive shaft assembly 84 with a conveying member 86 rotationally positioned there inside. The conveying member 86 receives the occlusion material cut by the cutting element 85 and transports the material along the chamber 82.

The drive shaft assembly 84 both transports cut tissue/material within the processing unit 80 and drives rotation of the cutting element 85. In other embodiments the drive shaft 84 may transport the cut tissue proximally within the processing unit 80 but may not drive rotation of a cutting element 85. FIG. 8 shows that the drive shaft assembly 84 is attached to the cutting element 85.

The drive shaft 84 is generally cylindrical and may comprise a solid tube or a hollow tube. The drive shaft with the conveying member 86 is manufactured to be flexible enough to facilitate navigation through tortuous vessel anatomy and strong enough to withstand the stresses encountered by high speed rotation, transmission of torque through the driveshaft to the cutter 85 at the distal tip of the processing unit 80, and transport occlusion material. The conveying member 86 may be a separate element which is attached or affixed in some manner to a substantially cylindrical drive shaft. Alternatively, the drive shaft 84 and the conveying member 86 may be formed as a single unitary element.

The drive shaft 84 is formed having a central lumen 88, which is used to deliver the guidewire 50, and may be coated with a lubricious material to avoid undesirable binding with the guidewire. The central lumen 88 of the shaft 84 may also be used to deliver fluids to the operative site simultaneously with or in place of the guidewire.

In one embodiment of the invention a plate 95 having a plurality of holes 97 passing from one face of the plate to the other is positioned within the chamber 82 transversely to the longitudinal axis thereof. In this manner, the occlusion material initially cut by the cutting member 85 is delivered by the conveying member 86 to the chamber 82 for further processing by passing through the plurality of holes 97 of the plate 95. The receiving chamber 82 along with the shaft 84 with the conveying member 86, and the optional plate 97 forms a first processing section 83 of the unit 80. Optionally it can be a second chamber 82'. Occlusion material from chambers 82/82' is pushed by the conveying member 86 to then space 52 through which the debris are vacuumed into the disposable storage located in the control unit.

The conveying member 86 may be an auger type system or an Archimedes-type screw that conveys the debris and cut material generated during the procedure away from the operative site. The conveying member 86 has raised surfaces or blades that drive materials away from the operative site. Blades of the conveying member 86 may extend up to a full diameter of the internal chamber 82 or a part of it.

Debris can be evacuated outside the body by the conveying member 86 action along the length of the catheter and with or without supplement of the vacuum pump connected to the catheter. Alternatively, the debris may be accumulated in a reservoir within the device.

Optionally, a plurality of generally equally spaced ridges 87, which can be collapsible in nature, are provided, extending from an inner wall 89 of the chamber. The ridges 87 tend to provide sufficient clearance about the conveying member 86. In this manner, initially processed occlusion materials can be propelled through the processing unit 80 without development of back pressure due to clogging in the assembly. The ridges 87 are aligned to increase material throughput rate by channeling material towards the proximal end of the unit 80.

As further illustrated in FIG. 8, optionally the tool of the invention can be provided with a second processing section 90. The second section 90 comprises a second chamber 82' with a second drive shaft 84' section having a conveying member 86' with a second pitch generally somewhat smaller than the pitch of the first conveying member 86. The first and second conveying members are co-axially arranged and formed with a longitudinally extending apertures used to accommodate, among other functions the hollow guidewire of the invention. The second section 90 can be optionally provided with a second plate 95' having a second plurality of holes 97' passing therethrough from one face thereof to the other. The holes 97' of the second plate 95' may be smaller than the holes of the first plurality of holes 97. In this manner, as previously discussed, the occlusion materials are initially processed by passage through the first plurality of holes 97 under the impetus of the first conveying member 86. Then, such initially processed material is further processed to a smaller size by passage through the second plurality of holes 97' under the impetus of the second conveying member 86'. The first and second conveying members can be formed as one unitary continuous structure or as two independent units. The debris are pushed by conveying member 86' through the opening 97' into space 52 connected with the vacuum in the control unit.

The second processing chamber can be employed in certain situations, for example, where highly calcified occlusion is encountered. In this instance, the material exiting the first plurality of holes can be in the form of relatively coarse agglomerations. Such material is then picked up and propelled by the second conveying member, so as to help to guide the material towards the second plate. As the cut material passes through the second plurality of holes of the second plate, further reduction of sizes of the occlusion particles takes place.

As illustrated in FIG. 8 the processing unit 80 can be optionally provided with the sleeve 60 slidably arranged at the exterior part of the catheter. In the illustrated expanded position, the sleeve 60 extends outwardly from the distal end of the unit 80. The hollow interior of the sleeve forms an interior space 64 that serves as a housing for the cutting element 85. An area of connection between the drive shaft and the cutting element 85 is also accommodated in the space 64. When the sleeve 60 is retracted in the proximal direction, the cutting element 85 is exposed.

In use when the sleeve 60 is in the expanded working position, the distal end 65 of the sleeve 60 engages the occlusion, then the cutting element 85 by the drive shaft is delivered through the interior space 64 to the operation site. The interior space 64 also creates a conduit which accommodates materials cut during the procedure and to improve the flow of various fluids during aspiration and/or infusion. In this embodiment the cutting element 85 is precisely delivered to the occlusion. Further, the walls of the sleeve 60 isolate the cutting element 85 from inner surfaces of the blood vessel walls to minimize the risk of accidental perforation/damage of the blood vessel walls.

In operation of the processing unit 80, initially the occlusion material cut by the cutting element 85 is processed and fed into the chamber 82. In the embodiment where the plate 95 is provided, the drive shaft assembly 84 having a conveying member 86 propels the cut occlusion material towards and through the holes 97. Thus, size of the initially cut occlusion materials is reduced to become more adaptable for suction, collection and disposal as previously discussed. To further reduce size of the cut occlusion materials, the second processing chamber 82' may be utilized in the above-discussed manner.

Application of the processing unit 80 combined with the cutting element 85 to many types of the intrabody surgery (as identified above) also forms a part of the invention. For example, in ureteroscopy procedure, which treats and removes stones in the kidneys and ureters, the processing unit 80 may be used in combination with the respective flexible scope. Use of the processing unit 80 is also applicable for larger stone removal, combined with RF cutting device, which passes through the scope to break stones up. Further, in the ureteroscopy the processing unit 80 can be used for the removal of polyps, tumors or abnormal tissue from a urinary tract. The processing unit 80 including the cutting element 85 is also usable in percutaneous nephrolithotomy or percutaneous nephrolithotripsy, combined with a small tube to reach the stone and break stone up with high-frequency sound waves or RF cutting device. Further, the processing unit 80 can be used in intrabody, laparoscopic and endoscopic orthopedic surgeries including but not limited to spine surgery, knee or hip replacement and similar. The processing, unit 80 can be used for safe and effective removal of any soft tissue. After the procedure the pieces are vacuumed up with a suction arrangement of the invention.

Turning now to FIG. 15 showing a processing unit 180 provided with a cutting assembly 185 at the distal end of the drive shaft 184. The assembly 185 is formed with a hub 160, a plurality of blades 162 arranged at an outer band 164 arranged at outer peripheries of the blades 162. In one embodiment, the hub, the blades and the outer band can be integrally formed. Each blade 162 is formed having a leading cutting edge 168 and a trailing edge 167, which extend in a plane generally perpendicular to axis of rotation. The outer band 164 has a front/distal area 166 facing the occlusion and a rear/proximal area. An abrasive cutting material is bonded or by any other conventional means attached to the distal area, forming an auxiliary cutting region 170. In the alternative, a cutting element or edge can be formed at the front area 166 of the outer band. Thus, the cutting assembly 185 is formed with two cutting regions, including the primary cutting region defied by the leading cutting edges 168 of the blades 162 and the auxiliary cutting region 170 defined the front area 166 of the outer band. In use, upon approaching the occlusion, the leading edges 168 of the primary cutting region remove or cut away a central area of the occlusion. On the other hand, tissues of the occlusion at the inner walls of the blood vessel are eliminated or cut away by the auxiliary cutting region 170. In the prior art procedures due to smaller outside diameter of the cutting tools relative to the inner diameter of the blood vessels and other reasons, such occlusion tissue often remains unremoved. Thus, application of the cutting assembly 185 of this embodiment enables a practitioner to eliminate or cut away the entire occlusion in one procedural step. This embodiment can be used for cutting soft occlusions tissues and is particularly applicable in stent restenosis procedures.

Similar to FIG. 8, the embodiment of FIG. 15 the processing unit 180 includes a chamber 182 with the drive shaft 184 provided with the conveying member 186. The drive shaft and the conveying member transport removed or cut tissue in the processing unit 180 and drive rotation of the cutting assembly 185. As illustrated in FIG. 15, the catheter is formed with an exterior sheath/to be shown/spaced from an inner hollow tube receiving the drive shaft. The drive shaft 184 is formed having the central lumen 188 used to deliver the guidewire 50 and may be also be used to deliver fluids to the operative site. To facilitate rotation of the drive shaft and the cutting assembly 185, the distal end/to be shown/of the processing unit 180 is separated from the cutting assembly 185 by a gap/to be shown/. Also, as illustrated in FIG. 15, the distal end can be flared. Furthermore, a lubricant can be delivered through the space separating the interior of the hollow tube and the drive shaft. The walls of the housing 180 may optionally expand to a higher diameter comparing with the average diameter of the catheter to accommodate a wider blade assembly 185 to optimally ablate occlusions in a larger diameter vessels.

The occlusion material cut by the cutting assembly 185 is delivered by the conveying member 186 to the chamber 182 for further processing, as previously discussed in the embodiment of FIG. 8. Then debris of processed cut material are evacuated through the space separating the exterior sheath from the inner tube with or without supplement of the vacuum pump connected to the catheter. Alternatively, the debris may be accumulated in a reservoir within the device.

Figure 9:
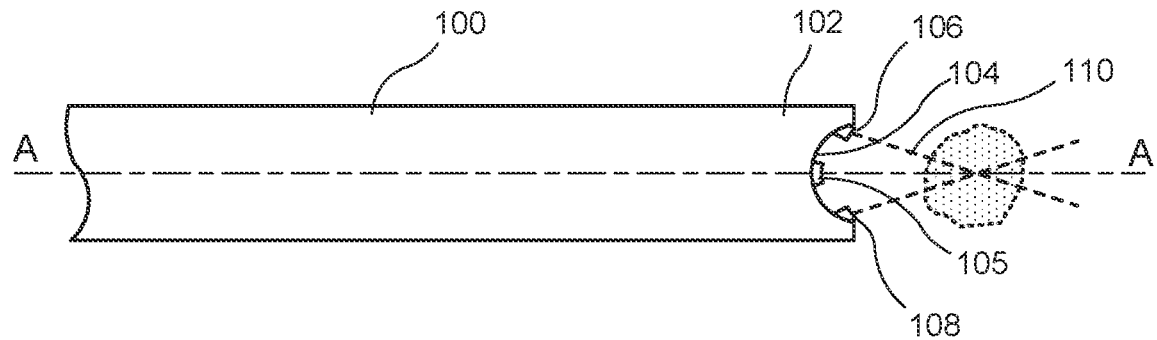
FIG. 9 is a diagram illustrating an embodiment of the invention utilizing ultrasound energy.

Turning now to FIG. 9 illustrating still another embodiment of the invention, wherein a source (generator) of ultrasound energy is disposed at the proximal end of the catheter. In the illustrated embodiment the source is in the form of a pair of spaced from each other ultrasound waive generators provided to generate ultrasound waves/beams focused on a specific area in the vicinity of the proximal end of the catheter. In use the proximal end is delivered to the occlusion, so that the ultrasound beams are focused to an area within the body of the occlusion for selective destruction of the occlusion tissue. Since the focus is spaced from the surrounding tissue, the risk of collateral damage to the surrounding blood vessels walls is minimized. Although a pair of cooperating ultrasound generators is shown, it should be appreciated however that the distal end of the catheter can be provided with any reasonable number of cooperating ultrasound generators.

As illustrated in FIG. 9, a distal end 102 of the catheter 100 is formed having a convex-shaped region 104 with one pair of the symmetrically arranged ultrasound energy generators 106 and 108. The convex-shaped region 104 reflects the energy emitted from the ultrasound generators and the beams 110 of the ultrasound energy are optimally focused at a specific/predetermined area within the body of the occlusion for a selective destruction of tissue. The focus of the beams 110 is disposed along the longitudinal axis A-A of the catheter and spaced from the distal end 102.

Optionally the distal end 102 of the catheter is made from a resilient material and the convex-shaped region 104 forms a suction cup, to further improve engagement between the distal end and the occlusion. This arrangement prevents spreading and facilitates catching of the debris. In addition, ultrasound energy detectors and/or other sensors 105, including but not limited to the temperature sensor, can be provided at the distal end 102 to control operation of ultrasound energy generators 106 and 108. The sensors/detectors 105 detect data related physical properties and chemical composition of the occlusion and transmit such data to the control unit. As previously discussed regarding FIG. 2, the computer or microchip 35 of the control unit 30 receives and analyzes the information obtained by the sensors/detectors 105 and generates a control signal to adjust functionality of the ultrasound energy generators 106 and 108, to optimize the destruction of an occlusion and produce other desired effects on targeted soft tissue.

Figure 10:
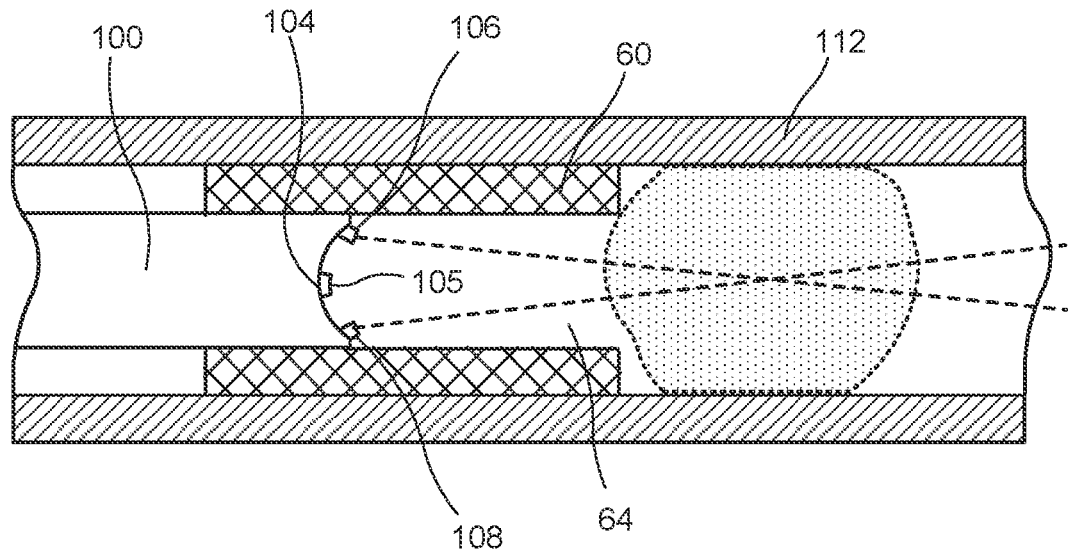
FIG. 10 is a section view of the embodiment shown in FIG. 9.

As illustrated in FIG. 10 the convex-shaped region 104 provided with the ultrasound energy generators 106, 108 can be used with the sleeve 60 slidably arranged at the exterior area of the catheter 114. In the illustrated expanded position, the hollow interior space 64 of the sleeve 60 serves as a housing for the convex-shaped region 104 including the ultrasound energy generators 106 and 108. In use the sleeve 60 is placed into the expanded, working position, and the distal end of the catheter with the ultrasound energy generators are delivered through the interior space 64 to the close proximity of the occlusion. In this manner, the ultrasound beams 110 are optimally focused at a specific area at the body of the occlusion for a selective destruction of the tissue. The interior space 64 of the sleeve 60 forms a conduit which accommodates materials cut during the procedure and improves the flow of various fluids during aspiration and/or infusion associated with use of the catheter. The convex-shaped region 104 with the ultrasound energy generators 106,108 are precisely delivered to the occlusion, and the walls of the sleeve further isolate the generators 106,108 from inner surfaces of the blood vessel walls 112, minimizing the risk of their accidental damage and/or perforation.

Figure 13:
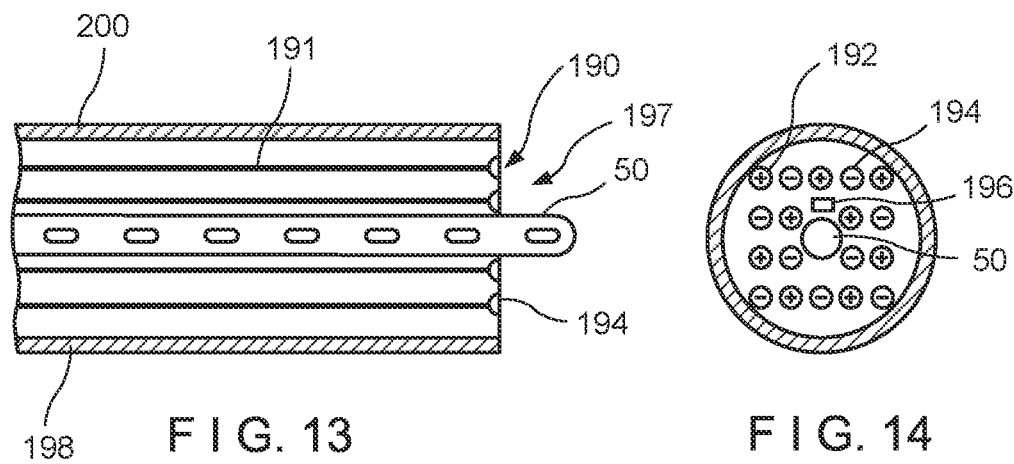
FIGS. 13 and 14 are diagrams illustrating still another embodiment of the invention utilizing RF energy.

Turning now to FIGS. 13 and 14 illustrating electro-surgical tool 190 according to a further embodiment of the invention. In this embodiment of the invention electro-surgical effects of ablation and resection are accomplished by applying a radio frequency (RF) current to the tissue through active electrodes (+) 192, from which the RF current flows to a ground or return (−) electrodes 194. As it passes through tissue from the active electrodes to the ground electrodes, the RF current cuts and/or coagulates the tissue, depending on power and wave length combinations. A flexible elongated hollow tubular body 200 is usually flexible and constructed of an electrically insulative material. Any of a number of polymeric or plastic materials may be employed for this purpose. The distal end 197 of the tool includes a plurality of the active electrodes and associated ground electrodes. A source (generator) of RF (radio frequency) energy (not shown) is disposed at the proximal end 198 of the tool or proximal end of the catheter in the control unit-power source. As illustrated in FIG. 13, in one application the catheter includes multiple electric wire conductors 191 longitudinally extending within a hollow interior of the body 200 to deliver electric current/voltage to the RF electrodes 192,194 provided at the distal end.

The ground electrodes (−) 194 are positioned close enough to the active (+) electrodes 192, so that the RF current flows a short distance. In this manner, loss of RF current by dissipation to the tissue and/or conductive irrigation fluids is reduced, and the desired effect or cutting performance of the tool 190 is not significantly degraded. In the bipolar instruments of the invention, the active electrodes 192 and the associated return electrodes 194 are disposed in close proximity to one another. So that there is less likelihood of current flow to tissues other than intended tissue being operated upon. Well-controlled bipolar RF energy delivery of the apparatus of this embodiment is preferred when ablating thinner or more delicate areas of tissue or when there is concern of possible collateral damage to target or non-target tissue.

As it shown in FIG. 13, the wire conductors 191 which deliver RF current to the electrodes are located within the interior cavity of the tubular body. The wire conductors and electrodes are designed so that they do not take up significant amount of the interior volume of the tubular body 200 and that the individual electrodes/wires do not interfere with each other. Open spaces formed within the catheter body between the wires and/or electrodes are used to evacuate ablated bodily material produced during the procedure. The evacuation can be accomplished, for example by a vacuum pump provided at the proximal end of the system creating allow-pressure zone resulted in suction pressure within the hollow inner space of the catheter, so that ablated bodily material directly removed from the operating site.

In an alternate embodiment, as illustrated in FIG. 13A electro-surgical tool 190 may also be constructed as a bipolar RF device with a single return/passive electrode 202 which is associated with a plurality of active electrodes disposed at the distal end of the body. The single passive electrode 202 is positioned at the distal end 196 of the catheter body in closely spaced relationship relative to the active electrodes. In one embodiment the single return/passive electrode 202 (see FIG. 13A, 14A) may be a unitary conductive ring positioned at the distal end of the catheter, completely of partially surrounding the distal end, with a surface area being substantially larger than that of any of the active delivery electrodes 192. It should be noted however that other shapes/forms/designs of the passive electrode are within the scope of the invention.

In an alternate embodiment (see FIG. 14 B) the conductive ring at the distal end of the catheter can be separated into a plurality of segments 205 forming multiplicity of return/passive electrodes 194 juxtaposed with individual active electrodes 192. These electrodes are in the form of metal sections/inserts electrically insulated from each other and completely of partially surrounding the distal end periphery. In this manner multiple bipolar tissue cutting segments are formed through entire cross-section of the tool 190.

The electrodes are positioned at the distal end, so that the electric current alternating between electrodes destroys the occlusion in contact with the electrodes. Because RF energy is delivered by means of electric current alternating between electrodes spaced/separated from inner areas of the blood vessel walls, application of RF technology provides higher safety compare to other methods. Therefore, possibility of damaging adjacent walls/tissues of blood vessels is minimized.

In a manner previously discussed, detector and/or sensor 196 can be provided at the distal end of the catheter for determining physical and chemical composition of the occlusion and by means of the computer or microchip of the control unit to adjust functionality of RF emitters.

The embodiment of FIGS. 9 and 10 was discussed with the source (generator) of ultrasound energy being disposed at the proximal end of the catheter. However, use of other energy generators is also within the scope of the invention. For example, the catheter can be provided with a cavitation source disposed at the distal end to deliver cavitation waves to be used in the intrabody surgery. In use the catheter passes through/positioned within the blood vessels (veins or arteries), so that such waves destroy or affect a soft tissue or an organ in a certain desirable way through mechanically or chemical-mechanical properties and/or forces. Outlets emitting cavitation energy can be added to the distal end of an existing catheter.

According to one embodiment of the invention the cavitation energy outlets are positioned on the outer diameter of the catheter tip and disposed at the longitudinal axis passing through the catheter. This facilitates focusing the cavitation waves at the central area of the occlusion. In this arrangement while the occlusions destroyed, the risk of damage to the blood vessel walls is substantially reduced or minimized.

As previously discussed, detector and/or sensor are provided at the distal end of the catheter capable determining physical and chemical composition of the occlusion and by means of the computer or microchip of the control unit to adjust performance of the cavitation energy outlets.

Figure 16A:
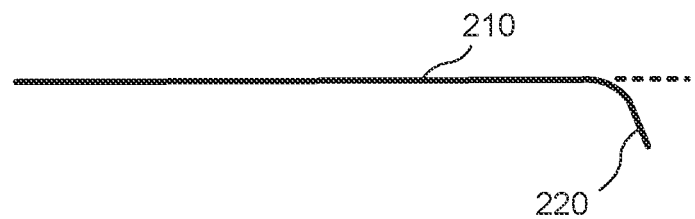
Figure 16B:
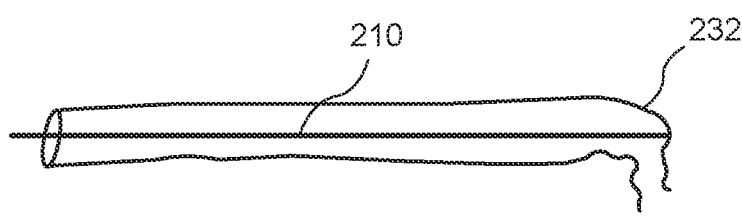
Figure 16C:
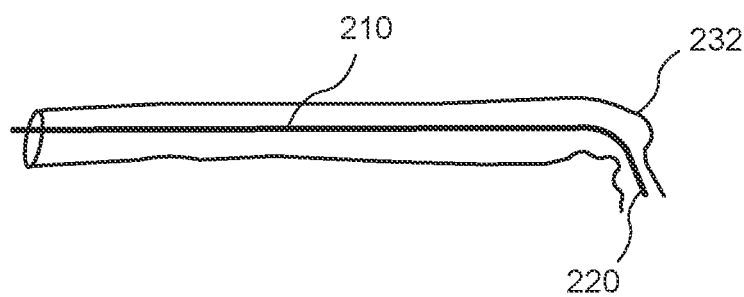

As illustrated on FIG. 16A a distal end 220 of a guidewire 210 can include a bend or curved portion which facilitates navigation of the guidewire in vasculature. Although various angles of inclination of the distal end to the remaining part of the guide wire are contemplated, in the preferred embodiment the distal end 210 is inclined at about 30-degree angle During the atherectomy procedure a guide wire is first installed into the vein or artery from the entre point of the patient body till the targeted occluded area of the targeted blood vessel. Such guidewire is designed to be thin and easy to pass within the blood vasculature. However, the longitudinal movement of the guidewire within the vessel is executed by the surgeon by pushing the guidewire forward along the blood vessel. For this movement to occur the guidewire must have certain stiffness which keeps it straight and prevent its coiling within the blood vessel. However, such stiffness in turn complicates the guidewire passing through the difficult vasculature with close to 90 degree or abuse angle of vessel curvature. Turning now to FIG. 16A showing that the very end section of the guidewire 220 can be bent to an optimum angle which may facilitate the guidewire passing through difficult angle vasculature. Surgeon can combine pushing of guidewire and rotating it so that the bended end of the guide wire may have a higher chance to slide into the difficult angle vessel while the straight end guidewire would just stop by pushing into the vessel wall. FIG. 16B shows a prior art straight guidewire inserted through the bore or lumen of a blood vessel 232 to cause a stop at the vessel wall making a sharp 90-degree turn. The bended end guidewire is utilized by the invention to facilitate the passing the sharp bend vascularity by providing an optional side direction for guide wire pushed forward by the surgeon. FIG. 16C illustrates a specific application of this feature of the invention, wherein 90-degree bended tip of the guidewire 220 is successfully pushed through by a main straight portion of the guidewire 210 through a 90 degree turn in vasculature.

Figure 17:
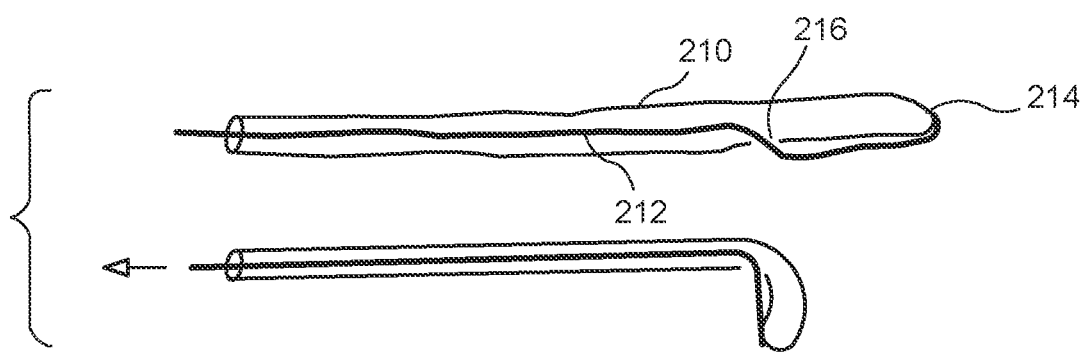
FIG. 17 illustrates an embodiment utilizing a pulling string or wire.

As illustrated on FIG. 17 a hollow guide wire 210 can also include a string 212 attached to the exterior part of the distal end 214. As further illustrated, the string 212 enters into the internal hollow part of the guidewire through a hole 216 located at predetermined optimal distance from the distal end. In this embodiment by pulling the string 212 an operator can remotely manipulate and/or bend the distal area of the guide wire 210 to an optimum angle thus targeting the distal end into required direction within the patient body lumens.

What is claimed is:

1. A surgical arrangement, comprising:
a body having a front region and a solid rear region having a semispherical shape, the front region formed by multiple spaced from each other longitudinal drilling sections extending along a longitudinal axis of the body interconnected by transversely oriented cutting sections, the drilling sections are positioned at an angle to each other defining in combination with the transversely oriented cutting sections a conically shaped grid formation culminating at a front tip; the grid formation defining a plurality of ports at intersection between the drilling sections and the cutting sections, an internal hollow cavity formed inside the grid formation with a channel having a central bore passing through the body; a low pressure zone formed within the hollow internal cavity, wherein debris of occlusion material are aspired by means of the low-pressure zone through the plurality of ports into the hollow internal cavity for further evacuation from the surgical arrangement.

2. The surgical arrangement of claim 1, wherein said rear region is connected to a distal end of a drive shaft which transmits torque to the surgical arrangement, the drive shaft is guided by a guidewire slidably disposed within the central bore, the ports connect an exterior of the front region with the internal cavity connected to the central bore and provide for aspiration of the debris resulted from drilling and cutting of the occlusion.

3. The surgical arrangement of claim 1, wherein the drilling sections and cutting sections are formed with sharp edges defining outer processing surfaces arranged to direct the debris into the internal cavity through the multiple ports.

4. The surgical arrangement of claim 3, wherein an abrasive material is bonded to exterior surfaces the longitudinal drilling sections and cutting sections.

5. The surgical arrangement of claim 1, wherein the cutting sections are asymmetrically arranged relative to the longitudinal axis of the body.

6. The surgical arrangement of claim 2, wherein the ports provide communication between the front region engaging an occlusion with the internal cavity and to provide communication with apertures provided in the guide wire.

7. The surgical arrangement of claim 2, wherein said solid semispherical rear region is formed with a substantially hollow interior extending between a distal part at a junction with the front region and a proximal part, a cross section of the distal part is greater than a cross section of the proximal part, a plurality of spaced from each other knifes provided at an inner surface of the hollow rear region interior, length of the knifes at the distal part being greater than length of the knifes at the proximal part, wherein in use said knifes further process the debris accumulated within the inner cavity by cutting and transporting the debris along the inner cavity to a hollow interior of the drive shaft.

8. The surgical arrangement of claim 7, wherein said knifes are arranged in at least two pairs opposing each other within the hollow rear region interior, so that said knifes of one pair are disposed between and face the knifes of another pair with tips of said knifes oriented toward the longitudinal axis of the body.

9. The surgical arrangement of claim 2, further comprising a connecting portion outwardly extending from the rear region, at least two arms each having a weight pivotally arranged within recesses formed in the connecting portion, wherein said arms and weights initially located within said recesses symmetrically relatively to the longitudinal axis, and upon being released by an operator one of the arms and the weights being pivoted away from the recess and the connecting portion upon to form a portion asymmetrical relative to the longitudinal axis.

10. The surgical arrangement of claim 1, further comprising an exterior shield spaced from and at least partially surrounding front cutting region and a substantially solid rear region preventing the materials developed during the surgery from being dispersed and to be directed into the interior cavity for evacuation from the surgical arrangement.

11. A surgical arrangement, comprising: a body having a front cutting region and a solid rear region having a semispherical shape, the front region formed by multiple spaced from each other longitudinal drilling sections extending along a longitudinal axis of the body interconnected by transversely oriented cutting blade sections, the drilling sections are positioned parallel to each other defining in combination with the transversely oriented cutting sections a cylindrically shaped grid formation; the grid formation defining a plurality of ports at intersection between the drilling sections and the cutting sections, an internal hollow cavity formed inside of the grid formation with a channel having a central bore passing through the body, a low pressure zone formed within the hollow internal cavity;

wherein debris of occlusion material are aspired by means of the low-pressure zone through the plurality of ports into the hollow internal for further evacuation from the surgical arrangement.

12. The surgical arrangement of claim 11, wherein said solid semispherical rear region is formed with a substantially hollow interior extending between a distal part at a junction with the front region and a proximal part, a cross section of the distal part is greater than a cross section of the proximal part, a plurality of spaced from each other knifes provided at an inner surface of the hollow rear region interior, length of the knifes at the distal part being greater than length of the knifes at the proximal part, wherein said knifes further process the debris of occlusion materials accumulated within the inner cavity by cutting and transporting the materials to a hollow interior of a drive shaft connected to said rear region.

13. The surgical arrangement of claim 12, wherein said knifes are arranged in at least two opposing each other pairs within the hollow rear region interior, so that said knifes of one pair are disposed between and face the knifes of another pair with tips of said knifes oriented toward the longitudinal axis of the body.

* * * * *